(12) United States Patent
Totey et al.

(10) Patent No.: US 7,674,620 B2
(45) Date of Patent: Mar. 9, 2010

(54) DERIVATION OF TERMINALLY DIFFERENTIATED DOPAMINERGIC NEURONS FROM HUMAN EMBRYONIC STEM CELLS

(75) Inventors: Satish Mahadeorao Totey, Maharashtra (IN); Geeta Ravindran, Maharashtra (IN)

(73) Assignee: Reliance Life Sciences Pvt. Ltd., Mumbai, Maharashtra (IN)

( * ) Notice: Subject to any disclaimer, the term of this patent is extended or adjusted under 35 U.S.C. 154(b) by 960 days.

(21) Appl. No.: 10/798,790

(22) Filed: Mar. 11, 2004

(65) Prior Publication Data

US 2006/0211109 A1   Sep. 21, 2006

Related U.S. Application Data

(60) Provisional application No. 60/520,048, filed on Nov. 14, 2003.

(51) Int. Cl.
C12N 5/06 (2006.01)
C12N 5/08 (2006.01)

(52) U.S. Cl. .................. 435/377; 435/363; 435/365; 435/368; 435/325

(58) Field of Classification Search .................. None
See application file for complete search history.

(56) References Cited

U.S. PATENT DOCUMENTS

| 5,514,552 | A | 5/1996 | Rosner et al. |
|---|---|---|---|
| 5,843,780 | A | 12/1998 | Thomson |
| 6,090,622 | A | 7/2000 | Gearhart et al. |
| 6,200,806 | B1 | 3/2001 | Thomson |
| 6,602,711 | B1 | 8/2003 | Thomson et al. |
| 2002/0009743 | A1 | 1/2002 | Carpenter |
| 2002/0019046 | A1 * | 2/2002 | Carpenter et al. ........... 435/368 |
| 2002/0039724 | A1 | 4/2002 | Carpenter |
| 2002/0068045 | A1 * | 6/2002 | Reubinoff et al. .......... 424/93.7 |
| 2002/0151053 | A1 | 10/2002 | Carpenter et al. |
| 2003/0036195 | A1 | 2/2003 | Studer et al. |
| 2003/0068819 | A1 | 4/2003 | Zhang et al. |
| 2003/0103949 | A1 | 6/2003 | Carpenter et al. |
| 2003/0104616 | A1 | 6/2003 | Parikh et al. |
| 2004/0014210 | A1 | 1/2004 | Jessell et al. |

FOREIGN PATENT DOCUMENTS

| WO | WO 01/51616 | 7/2001 |
|---|---|---|
| WO | WO 01/83715 | 11/2001 |
| WO | WO 01/88104 | 11/2001 |
| WO | WO 02/086073 | 10/2002 |
| WO | WO 03/000868 | 1/2003 |
| WO | WO 03/104444 | 12/2003 |
| WO | WO 2004/015077 | 2/2004 |

OTHER PUBLICATIONS

Martina Böttner, et al., *The Transforming Growth Factor-βs: STructure, Signaling, and Roles in Nervous System Development and Functions*, Journal of Neurochemistry, 75(6):2224-2240, 2000.
PCT/IB04/01246, International Search Report, Nov. 1, 2005.
Åkerud et al., "Neuroprotection through Delivery of Glial Cell Line-Derived Neurotrophic Factor by Neural Stem Cells in a Mouse Model of Parkinson's Disease." *J. Neurosci.* 21:8108-8118 (2001).
Bain et al., "Embryonic Stem Cells Express Neuronal Properties in Vitro." *Developmental Biology 168*: 342-357 (1995).
Björklund et al., "Embryonic Stem Cells Develop Into Functional Dopaminergic Neurons After Transplantation in a Parkinson Rat Model." *PNAS* 99:2344-2349 (2002).
Björklund et al., "Reinnervation of the Denervated Striatum by Substantianigra Transplants: Functional Consequences as Revealed by Pharmacological and Sensorimotor Testing." *Brain Research* 199:307-333 (1980).
Brundin et al., "Intracerebral Grafting of Dopamine Neurons." Ann. N.Y. Acad. Sci. 495:473-496 (1987).
Brüstle et al., "Embryonic Stem Cell-Derived Glial Precursors: A Source of Myelinating Transplants." Science Magazine 285:754-56 (1999).
Buehr et al., "Mesonephric Contribution to Testis Differentiation in the Fetal Mouse." Development 117:273-281 (1993).
Damjanov et al., "Retinoic Acid-Induced Differentiation of the Developmentally Pluripotent Human Germ Cell Tumor-Derived Cell Line, NCCIT." Laboratory Investigation 68:220-232 (1993).
Dunnett et al., "Behavioural Recovery Following Transplantation of Substantia Nigra in Rats Subjected to 6-OHDA Lesions of the Nigrostriatal Pathway .I. Unilaterial Lesions." Brain Research 215:147-161 (1981).
Dunnett et al., "*Intracerebral Grafting of Neuronal Cell Suspensions v. Behavioural Recovery in Rats with Bilateral 6-OHDA Lesions Following Implantation of Nigral Cell Suspensions.*" Acta Physiol. Scan. Suppl. 522:39-47 (1983).
Eriksson et al., "Neurogenesis in the Adult Human Hippocampus." Nature America, Inc. 4:1313-1317 (1998).
Freed et al., "Transplantation of Embryonic Dopamine Neurons for Severe Parkinson's Disease." New England Journal of Medicine 344:710-19 (2001).

(Continued)

*Primary Examiner*—David S Romeo
*Assistant Examiner*—Daniel C Gamett
(74) *Attorney, Agent, or Firm*—Vinson & Elkins LLP

(57) ABSTRACT

The present disclosure is directed to improved methods for efficiently producing neuroprogenitor cells and differentiated neural cells such as dopaminergic neurons and serotonergic neurons from pluripotent stem cells, for example human embryonic stem cells. Using the disclosed methods, cell populations containing a high proportion of cells positive for tyrosine hydroxylase, a specific marker for dopaminergic neurons, have been isolated. The neuroprogenitor cells and terminally differentiated cells of the present disclosure can be generated in large quantities, and therefore may serve as an excellent source for cell replacement therapy in neurological disorders such as Parkinson's disease.

28 Claims, 13 Drawing Sheets

OTHER PUBLICATIONS

Henderson et al., "Neurotrophic Factors in Development and Plasticity of Spinal Neurons." Restorative Neurology and Neuroscience 5:15-28 (1993).

Hofer and Barde, "Brain-derived Neurotrophic Factor Prevents Neuronal Death in vivo." Nature 331:261-262 (1988).

Kawasaki et al., "Induction of Midbrain Dopaminergic Neurotechnique Neurons from ES Cells by Stromal Cell-Derived Inducing Activity." Neuron 28:31-40 (2000).

Kim et al., "Dopamine Neurons Derived from Embryonic Stem Cells Function in an Animal Model of Parkinson's Disease." Nature 418:50-56 (2002).

Kukekov et al., "Multipotent Stem/Progenitor Cells with Similar Properties Arise From Two Neurogenic Regions of Adult Human Brain." Exper. Neurology 156:333-344 (1999).

Lauder and Bloom, "Ontogeny of Monoamine Neurons in the Locus Coeruleus, Raphe Nuclei and Substantia Nigra of the Rat." J. Comp. Neur. 155:469-481 (1974).

Lee et al., "Efficient Generation of Midbrain and Hindbrain Neurons From Mouse Embryonic Stem Cells." Nature Biotech. 18:675-679 (2000).

Lin et al., "GDNF: A Glial Cell Line-Derived Neurotrophic Factor for Midbrain Dopaminergic Neurons." Science 260:1130-32 (1993).

Lin et al., "Purification and Initial Characterization of Rat B49 Glial Cell Line-Derived Neurotrophic Factor." Jour. of Neurochem. 63:758-768 (1994).

Nadaud et al., "Functional Recovery Following Transplantation of Ventral Mesencephalic Cells in Rat Subjected to 6-OHDA Lesions of the Mesolimbic Dopaminergic Neurons." Brain Research 304:137-141 (1984).

Reubinoff et al., "Embryonic Stem Cell Lines From Human Blastocysts: Somatic Differentiation in vitro." Nature Biotech. 18:399-404 (2000).

Reynolds and Weiss, "Generation of Neurons and Astrocytes From Isolated Cells of the Adult Mammalian Central Nervous System." Science 255:1707-1710 (1992).

Rolletschek et al., "Differentiation of Embryonic Stem Cell-Derived Dopaminergic Neurons is Enhanced by Survival-Promoting Factors." Mech. Dev. 105:93-104 (2001).

Rosenthal, "Auto Transplants for Parkinson's Disease?" Neuron 20:169-172 (1998).

Shamblott et al., "Derivation of Pluripotent Stem Cells From Cultured Human Primordial Germ Cells." Proc. Natl. Acad. Sci. 95:13726-13731 (1998).

Strömberg et al., "Glial Cell Line-Derived Neurotrophic Factor is Expressed in the Developing but Not Adult Striatum and Stimulates Developing Dopamine Neurons in vivo." Experimental Neurology 124:401-412 (1993).

Svendsen et al., "Long-Term Survival of Human Central Nervous System Progenitor Cells Transplanted into a Rat Model of Parkinson's Disease." Experimental Neurology 148:135-146 (1997).

Thomson et al., "Embryonic Stem Cell Lines Derived from Human Blastocysts." Science 282:1145-47 (1998).

Thomson et al., "Isolation of a Primate Embryonic Stem Cell Line." Proc. Natl. Acad. Sci. 92:7844-7848 (1995).

Thomson and Marshall, "Primate Embryonic Stem Cells." Dev. Biology 38:133-165 (1998).

Vescovi et al., "Isolation and Cloning of Multipotential Stem Cells from the Embryonic Human CNS and Establishment of Transplantable Human Neural Stem Cell Lines by Epigenetic Stimulation." Exper. Neurology 156:71-83 (1999).

Vescovi et al., "Isolation and Intracerebral Grafting of Nontransformed Multipotential Embryonic Human CNS Stem Cells." Journal of Neurotrauma 16:689-693 (1999).

Winkler et al., "Transplantation in the Rat Model of Parkinson's Disease: Ectopic Versus Homotopic Graft Placement." Progress in Brain Research 127:233-265, (2000).

Yurek and Sladek, "Dopamine Cell Replacement: Parkinson's Disease." Annu. Rev. Neurosci. 13:415-40 (1990).

Zhang et al., "In vitro Differentiation of Transplantable Neural Precursors From Human Embryonic Stem Cells." Nature Biotech. 19:1129-1133 (2001).

* cited by examiner

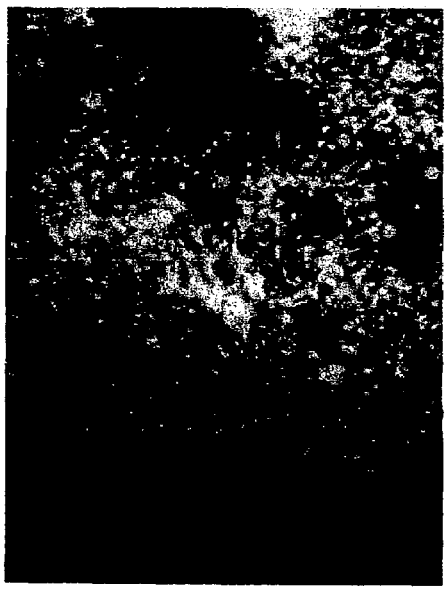 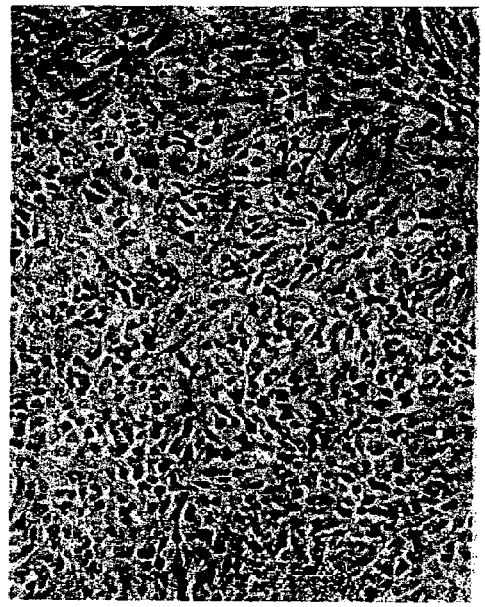
Figure.1: A- Nestin positive cells;
B- Expansion of Nestin positive cells

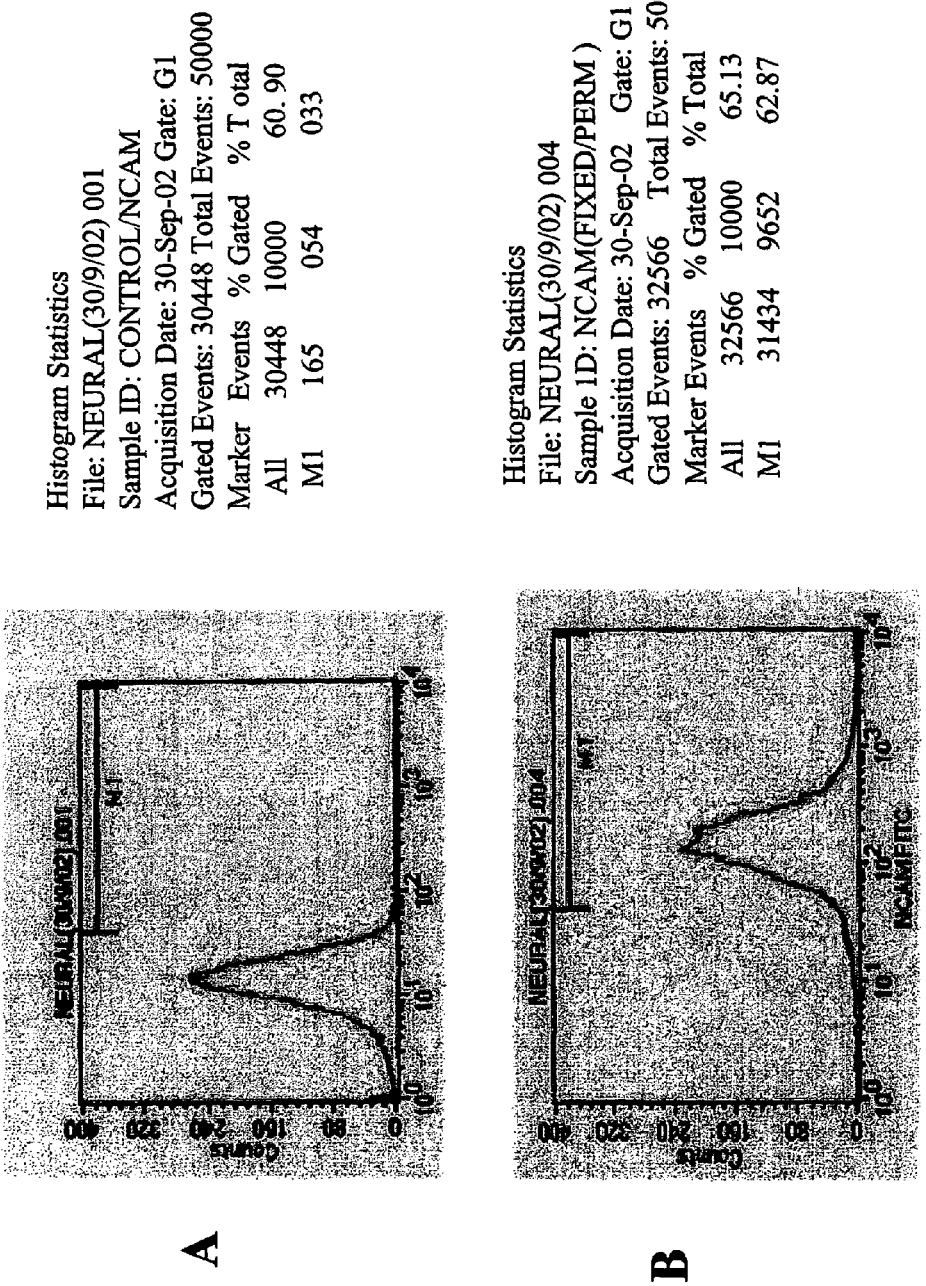
Figure.2: FACS analysis
A-Control (unlabelled cells)
B- NCAM positive cells

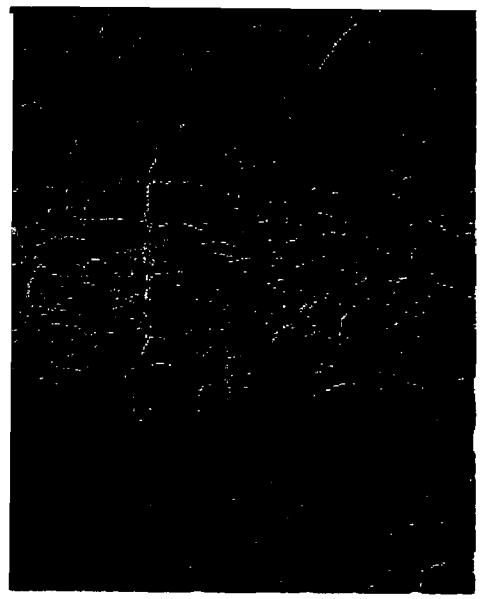
Figure. 3: Magnetic Sorting of NCAM positive cells
A, B- NCAM positive cells

Figure.4A : MAP-2 positive cells
Figure.4B : βTubulin positive cells

A
B
Figure.5 : Cells positive for Tyrosine hydroxylase

Figure.6 Oligodendrocyte
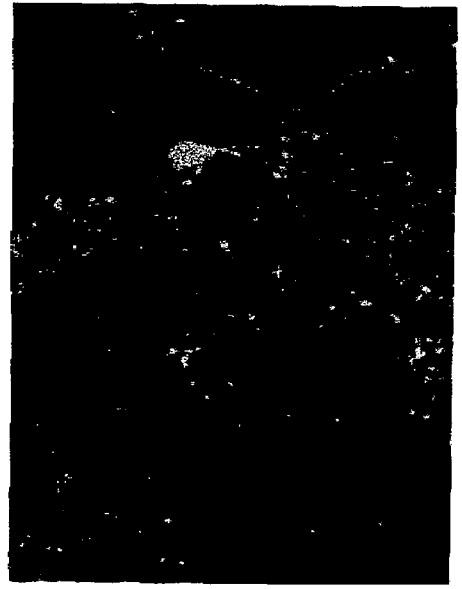
Figure.7 Serotonin

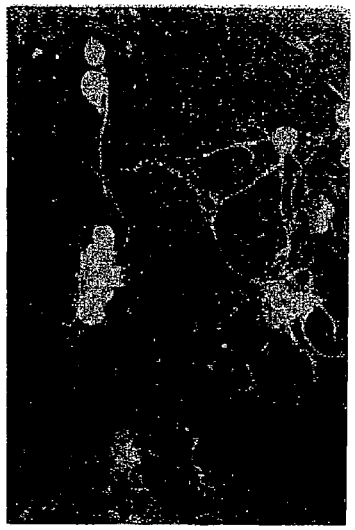 TH/MAP-2
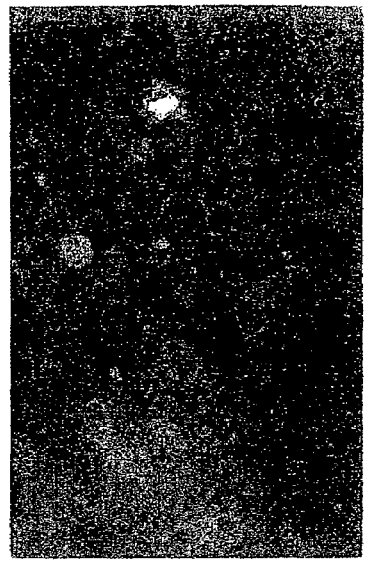 TH/DAT
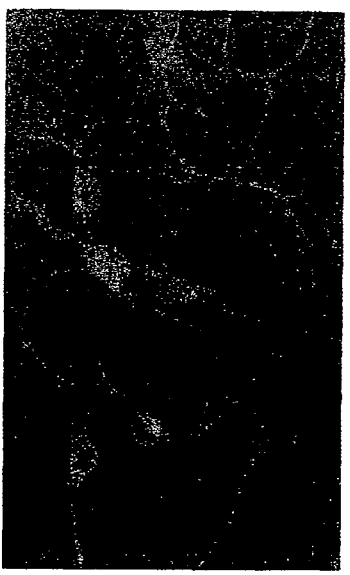 TH / β tubulin
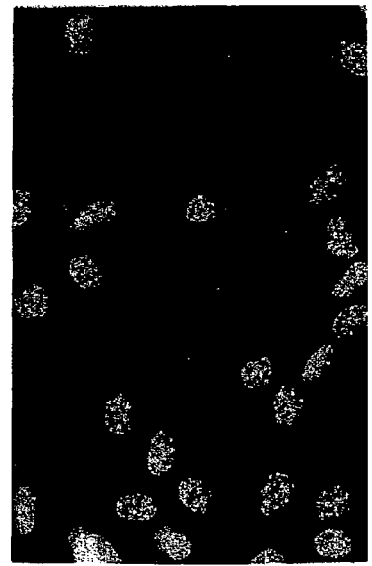 TH/Nurr1
Figure. 8. Co-localisation of TH with other neuronal antigens

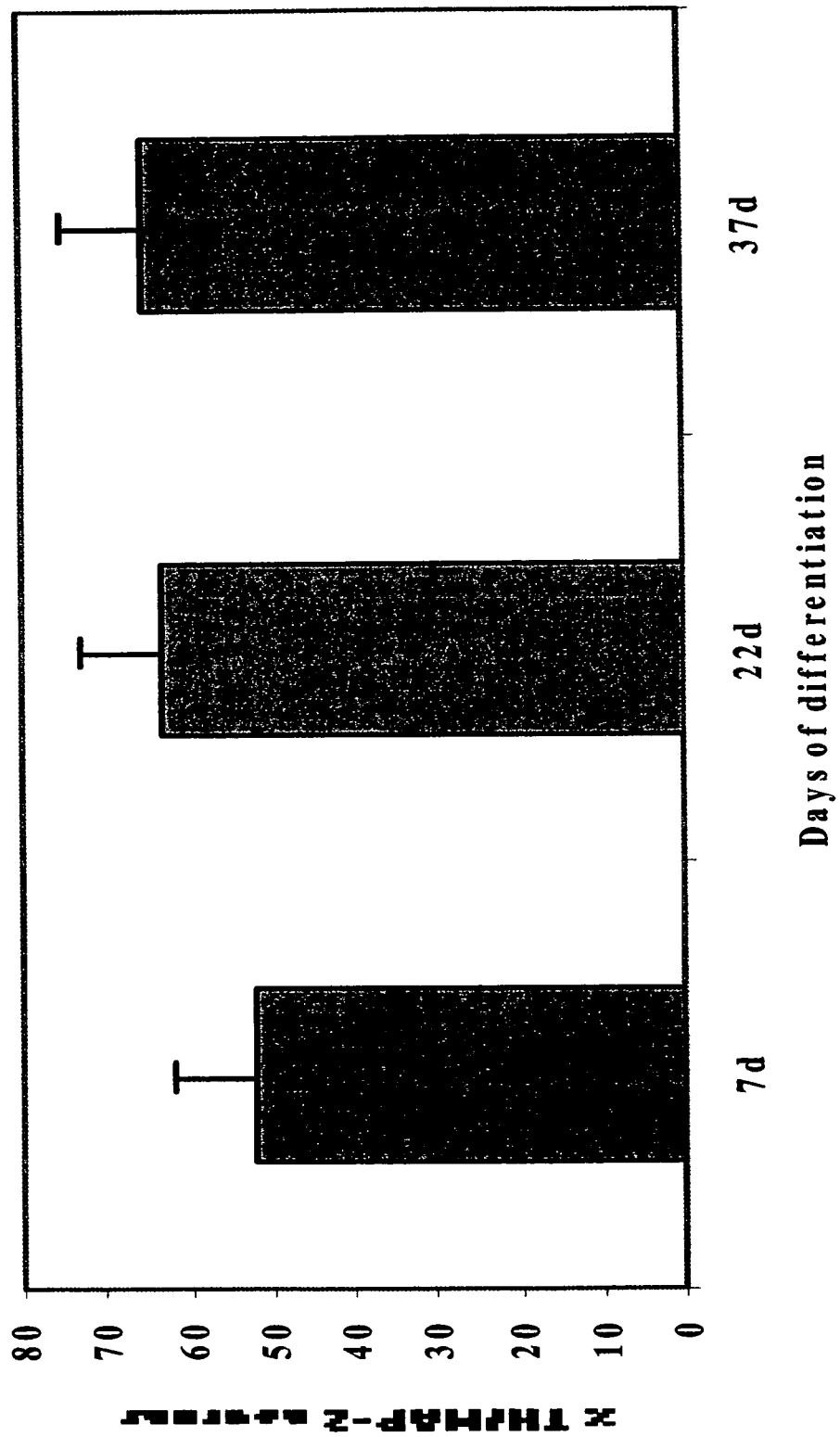
Figure 9: Percent proportion of TH positive neurons

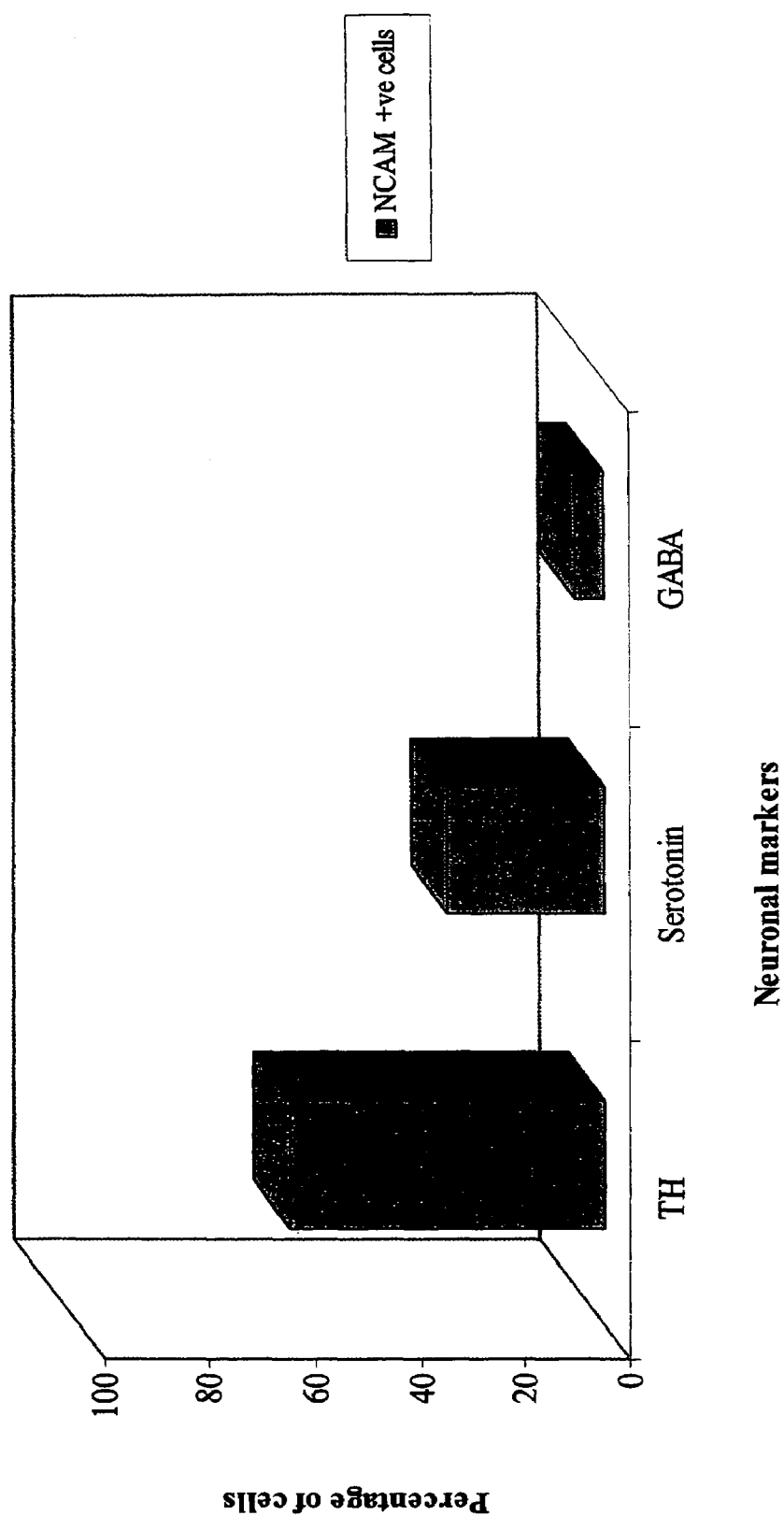
Figure 10: Quantitative analysis of neuronal populations from NCAM enriched cells. Tyrosine hydroxylase positive cells found to be 60%

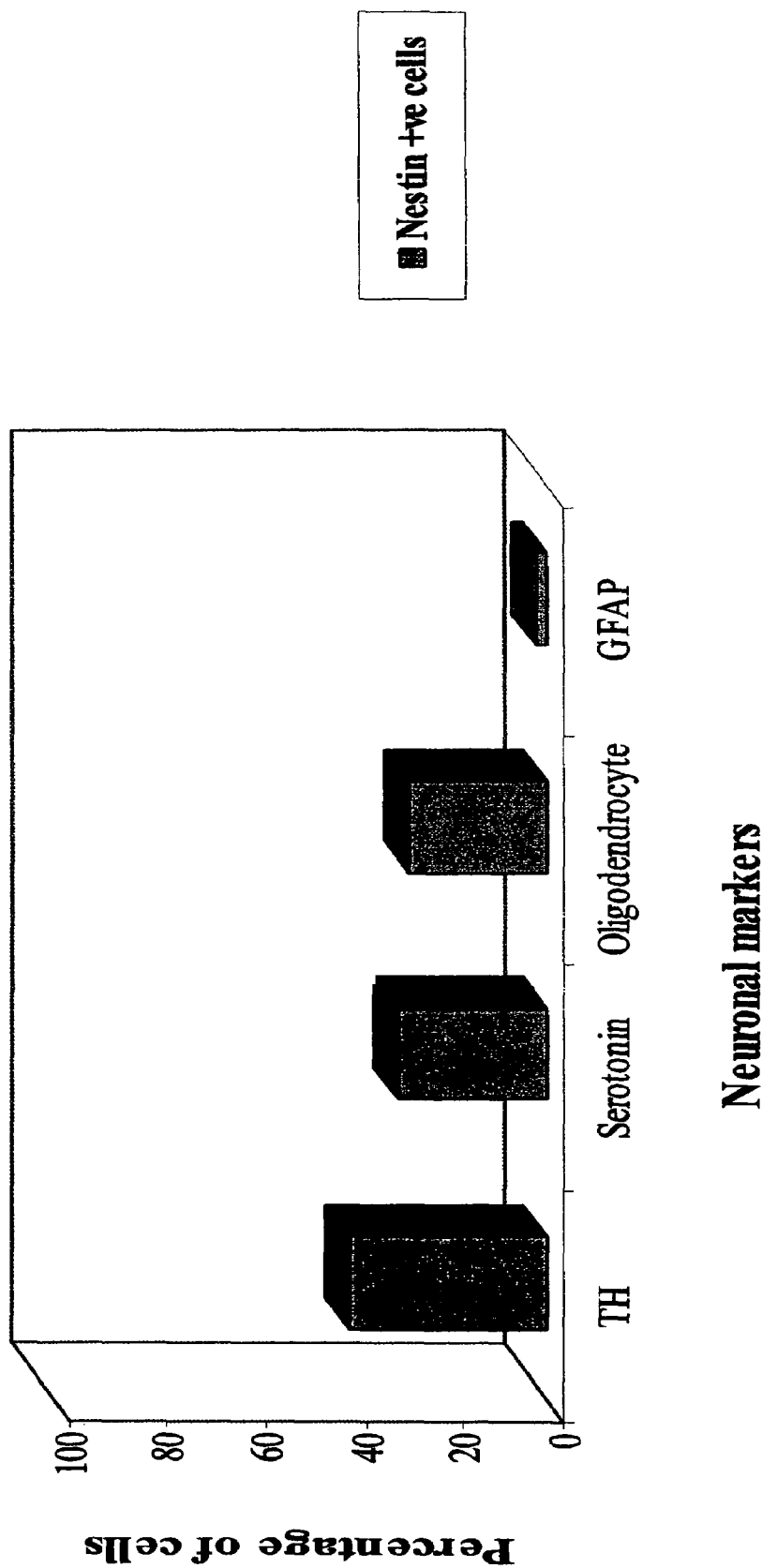
Figure 11: Quantitative analysis of neuronal populations from Nestin expansion and differentiation. Tyrosine hydroxylase positive cells found to be 40%

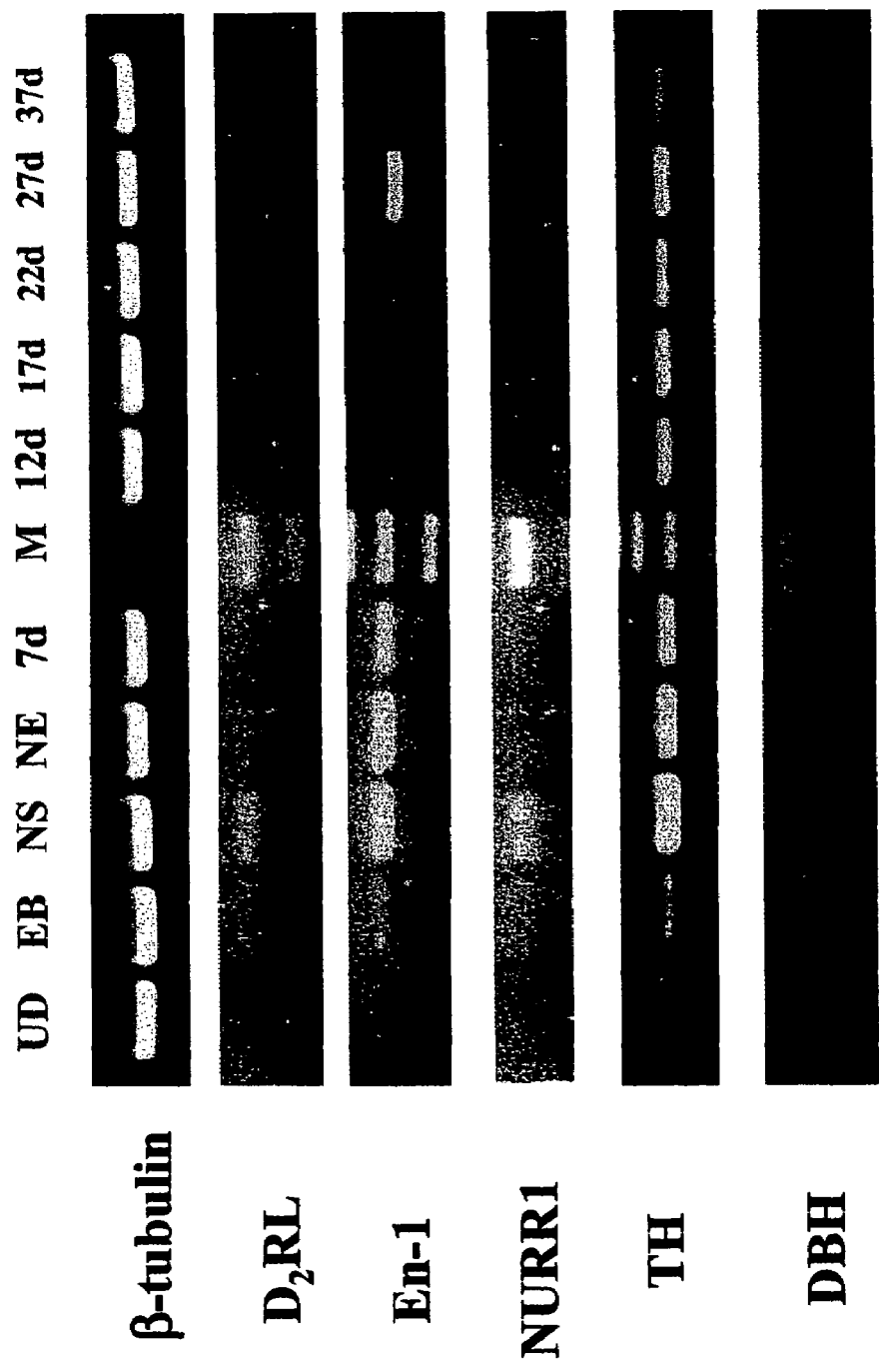
Figure. 12 : Expression of Dopamine specific genes in ES derived neurons

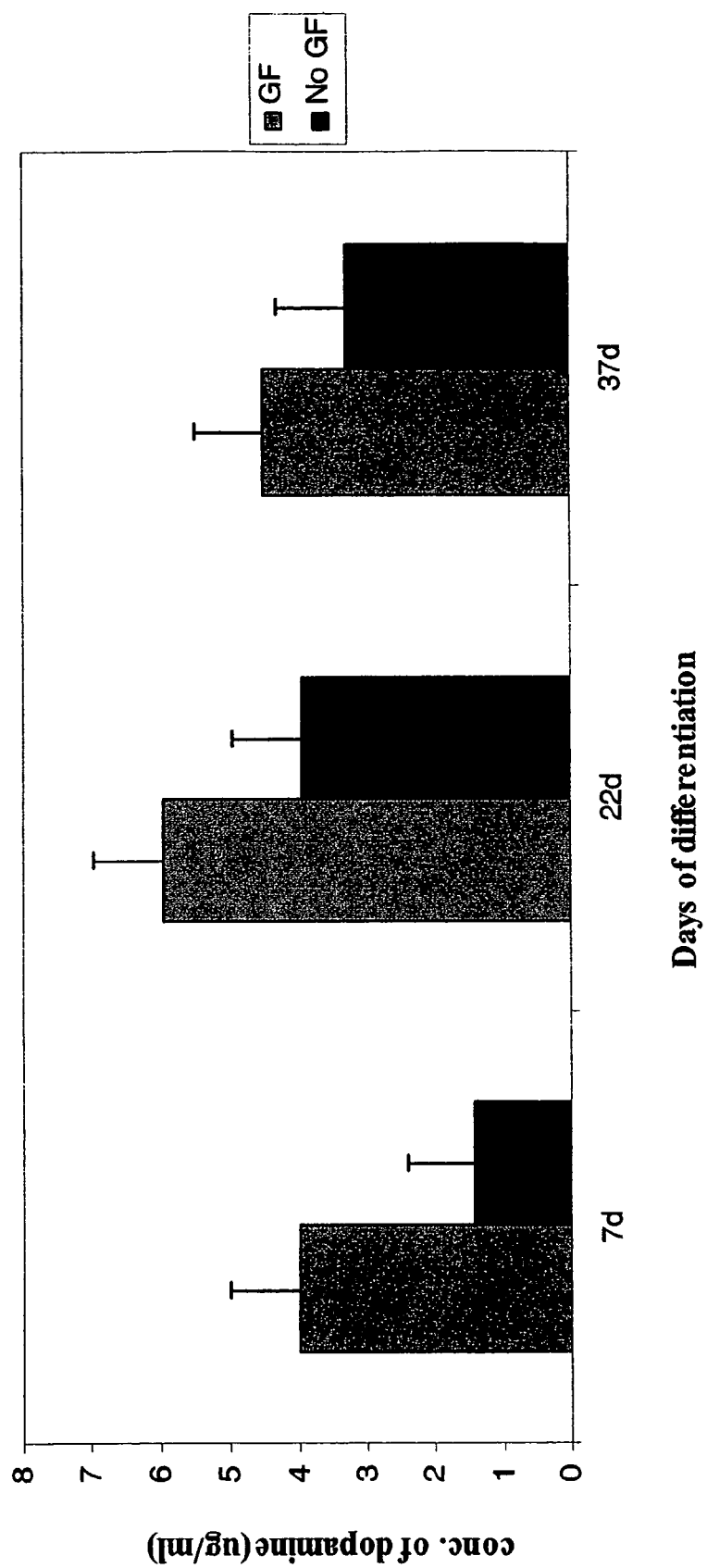
Figure. 13 : Analysis of intracellular dopamine in cell lysates

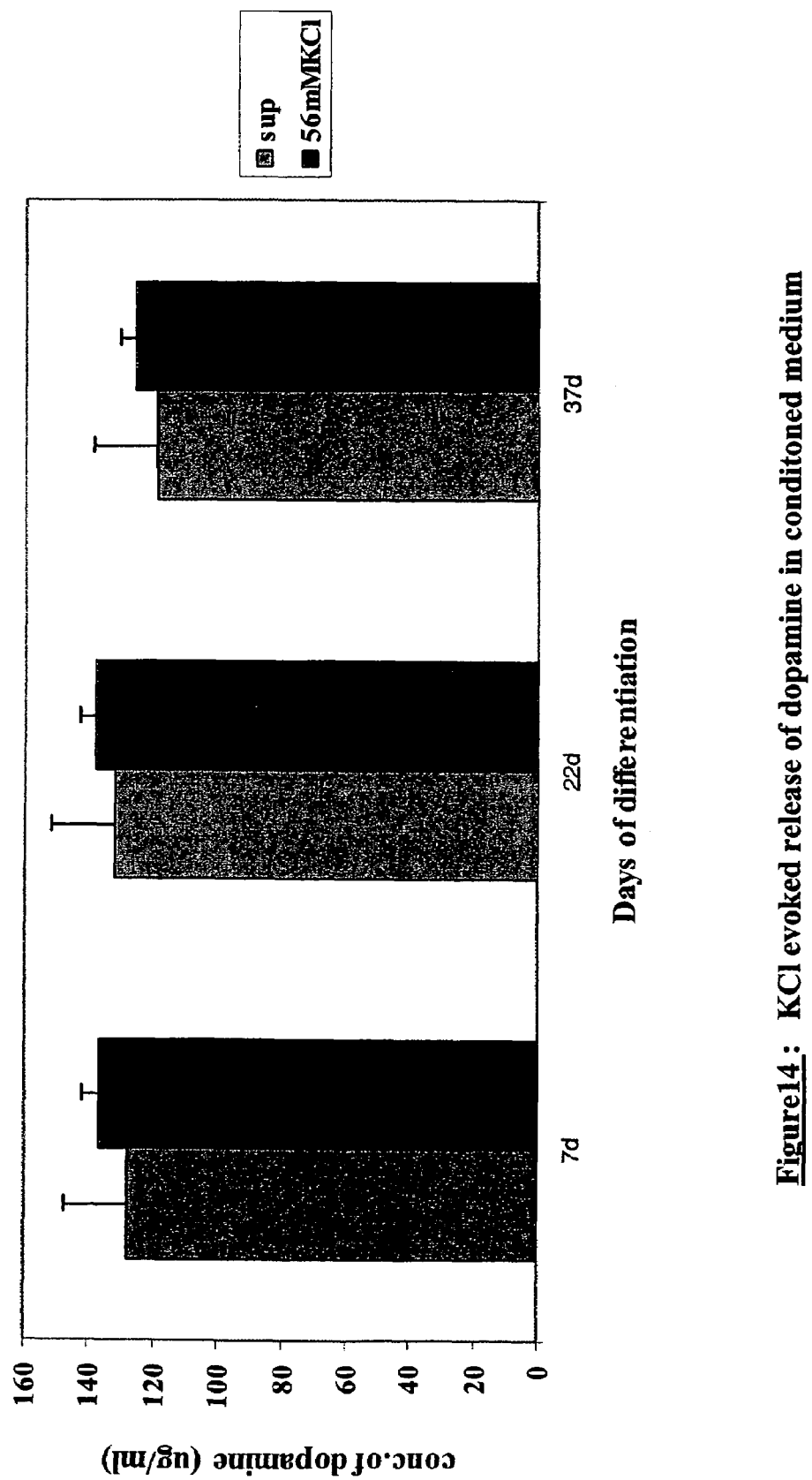
Figure 14 : KCl evoked release of dopamine in conditoned medium

SEQUENCE LISTING

<160> NUMBER OF SEQ ID NOS: 12

<210> SEQ ID NO 1
<211> LENGTH: 20
<212> TYPE: DNA
<213> ORGANISM: Homo sapiens

<400> SEQUENCE: 1
tgtcagagca gcccgaggtc                                              20

<210> SEQ ID NO 2
<211> LENGTH: 20
<212> TYPE: DNA
<213> ORGANISM: Homo sapiens

<400> SEQUENCE: 2
ccaagagcag cccatcaaag                                              20

<210> SEQ ID NO 3
<211> LENGTH: 20
<212> TYPE: DNA
<213> ORGANISM: Homo sapiens

<400> SEQUENCE: 3
gcagtcgagc tttcagagcc                                              20

<210> SEQ ID NO 4
<211> LENGTH: 21
<212> TYPE: DNA
<213> ORGANISM: Homo sapiens

<400> SEQUENCE: 4
tctgcggctc atcgtcttaa g                                            21

<210> SEQ ID NO 5
<211> LENGTH: 26
<212> TYPE: DNA
<213> ORGANISM: Homo sapiens

<400> SEQUENCE: 5
cacgtactgg tgctacatta aggagc                                       26

<210> SEQ ID NO 6
<211> LENGTH: 26
<212> TYPE: DNA
<213> ORGANISM: Homo sapiens

<400> SEQUENCE: 6
aatggccatc actggcgtgt aacacc                                       26

<210> SEQ ID NO 7
<211> LENGTH: 22
<212> TYPE: DNA
<213> ORGANISM: Homo sapiens

<400> SEQUENCE: 7
tggtcaagac tgactcacag ca                                           22

<210> SEQ ID NO 8
<211> LENGTH: 22
<212> TYPE: DNA
<213> ORGANISM: Homo sapiens

```
-continued

<400> SEQUENCE: 8
tctcgtcttt gtcctgaacc gt                                              22

<210> SEQ ID NO 9
<211> LENGTH: 22
<212> TYPE: DNA
<213> ORGANISM: Homo sapiens

<400> SEQUENCE: 9
tgaagagagc ggagaaggag at                                              22

<210> SEQ ID NO 10
<211> LENGTH: 23
<212> TYPE: DNA
<213> ORGANISM: Homo sapiens

<400> SEQUENCE: 10
tctggagtta agaaatcgga gct                                             23

<210> SEQ ID NO 11
<211> LENGTH: 20
<212> TYPE: DNA
<213> ORGANISM: Homo sapiens

<400> SEQUENCE: 11
ggaacatagc cgtaaactgc                                                 20

<210> SEQ ID NO 12
<211> LENGTH: 20
<212> TYPE: DNA
<213> ORGANISM: Homo sapiens

<400> SEQUENCE: 12
tcactgtgcc tgaacttacc                                                 20
```

DERIVATION OF TERMINALLY DIFFERENTIATED DOPAMINERGIC NEURONS FROM HUMAN EMBRYONIC STEM CELLS

CROSS-REFERENCES TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present disclosure relates to an improved method of producing terminally differentiated neuronal cells such as dopaminergic and serotonergic neurons from pluripotent embryonic stem cells such as human embryonic stem cells. The dopaminergic and serotonergic neurons generated according to the present disclosure may serve as an excellent source for cell replacement therapy in neurodegenerative disorders and neuronal diseases.

2. Description of Related Art

Neurodegenerative disorders and neuronal diseases such as Parkinson's disease, Alzheimer's disease, and schizophrenia are destructive diseases that are becoming ever more prominent in our society. Many of these neurological disorders are associated with dopaminergic or serotonergic neurons. Dopaminergic neurons reside in the ventral and ventro-lateral aspects of the midbrain, and control postural reflexes, movement, and reward-associated behaviors. These neurons innervate multiple structures in the forebrain, and their degeneration or abnormal function is associated with Parkinson's disease, schizophrenia, and drug addiction (Hynes et al., 1995, Cell 80:95-101). Serotonergic neurons are concentrated in the ventral and ventro-lateral aspects of the hindbrain and innervate most parts of the central nervous system including the cerebral cortex, limbic system and spinal cord. These neurons control levels of awareness, arousal, behavioral traits, and food intake, and their abnormal function has been linked to aggression, depression, and schizophrenia (Jacobs and Gelperin, 1981, Serotonin Neurotransmission and Behavior. The MIT Press, Cambridge, Mass.). Serotonergic dysfunction may also play a role in the pathophysiology of various psychiatric, neurologic, and other diseases, for example, mental depression (Asberg et al., 1986, J. Clin. Psychiatry 47:23-35), suicide (Lester, 1995, Pharmocopsychiatry 28(2):45-50), and violent aggressive behavior (Brown et al., J. Clin. Psychiatry, 1990, 54:31-41; Eichelman, 1990, Annu. Rev. Med. 41:149-158).

Parkinson's disease is a progressive neurological disorder caused by the degeneration of nerve cells (neurons) in the region of the brain that controls movements. This degeneration creates a shortage of the brain signaling chemical (neurotransmitter) known as dopamine, causing the movement impairments that characterize the disease. Pathological studies indicate that loss of dopaminergic neurons in the substantia nigra contributes to Parkinson's disease. For example, bilateral lesions of the nigrostriatal pathway produce a syndrome in experimental animals that is quite similar to the observed motor dysfunctions observed in Parkinson's disease: resting tremor, rigidity, akinesia and postural abnormalities. Bilateral lesions of the nigrostriatal pathway caused by 6-hydroxydopamine (OHDA) caused profound akinesia, adipsia, aphagia and sensory neglect in rodents (Ungerstedt, 1971, U. Acta Physiol. Scand. Suppl. 367:95-121; Yirek and Sladek, 1990, Annu. Rev. Neurosci. 13:415-440).

In parkinsonism, changes in the status of dopaminergic receptors may be dependent on the stage of progression of the disease. The hallmark of parkinsonism is a severe reduction of dopamine in all components of the basal ganglia (Hornykiewicz, 1988, Mt. Sinai J. Med. 55:11-20). When dopamine is depleted, various other areas in the brain such as the thalamus, globus pallidus, and the subthalamic nucleus start to malfunction. Since these areas send signals to other parts of the brain, malfunctions in these small areas can lead to widespread brain dysfunction.

The prevalence of Parkinson's disease varies widely from 82 per 100,000 in Japan and 108 per 100,000 in UK, to nearly 1% (approximately 1 million) of the population in North America. In India, the prevalence rate of Parkinson's disease is 14 per 100,000 in North India, 27 per 100,000 in South India, 16 per 100,000 in East India, and 363 per 100,000 for the Parsi community in Western India. While Parkinson's disease is currently considered incurable, a variety of medications are available that provide symptomatic relief from Parkinson's disease, including Levodopa, Bromocriptine, pergolide, selegiline, anticholinergic, and amantadine. Although these drugs may provide relief from the symptoms of Parkinson's disease, they often have significant side effects. Moreover, these drugs neither cure the disease nor slow down the progressive loss of neurons, and only relieve the symptoms, with the beneficial effects often wearing off with time. Some patient become less responsive to medication, while others become hypersensitive and develop dyskinesias.

These unsatisfactory outcomes have led to development of other strategies for treating this disease, such as dopa-receptor agonist therapy and surgical approaches that include pallidotomy, deep brain stimulation (DBS) of the globus pallidus, and attempts to interrupt network abnormalities by destroying overactive brain areas or placing DBS electrodes to quiet these area. Although these and other types of surgery for patients with Parkinson's disease patients have produced some beneficial results, the long-term effects of such surgeries are not yet known. These treatments also have certain limitations and side effects.

Another strategy being pursued for this incurable disease is gene therapy. Discovery of the molecular basis of neurological disease and advances in gene transfer systems have allowed focal and global delivery of therapeutic genes for a wide variety of central nervous system disorders. But gene therapy has certain limitations such as stability and regulation of transgene expression, and safety of both vector and expressed transgenes (Costantini et al., 2000, Gene Therapy 7: 93-109). Vectors shown to be used for gene therapy include but are not limited to Herpes Simplex Virus type-1 (HSV-1) (During et al., 1994, Science 266:1399-1403), adeno-associated virus vector (AAV) (During et al., 1998, Gene Therapy 5:820-827), retrovirus, HSV/Epstein-Barr Virus (HSV/EBV) hybrid vector, and HSV/AAV hybrid vector. One gene therapy approach has been found useful to treat an animal model of Parkinson's disease. An encapsulated, genetically engineered cell line releasing the neuroprotective molecule, glial cell line-derived neurotrophic factor gene (GDNF), and a lentiviral vector encoding the GDNF gene improved graft survival and differentiation, thereby accelerating behavioral recovery in the animal model (Zurn et al., 2001, Brain Res Rev. 36:222-229; Date et al., 2001, Cell Transplant 10:397-401). Gene therapy using neural stem cells has also been found to be effective in expressing therapeutic levels of GDNF in vivo (Akerud et al., 2001. J. Neurosci. 21:8108-8118).

Cell implantation is another therapeutic strategy that offers the hope of replacing nerve cells lost in Parkinson's disease, as well as other neurodegenerative disorders and neuronal diseases. Clinical trials with fetal tissue transplantation, still underway, have developed methods for implanting cells into the brain and demonstrated the viability of this concept, as well as produced promising results for at least some patients. Attempts have also been made to transplant precursors of dopaminergic nerve cells directly into the striatum of patients with Parkinson's disease, and transplantation of human fetal or embryonic dopaminergic neurons have been found to have a beneficial effect on patient with Parkinson's disease (Freed et al., 2001, N. Engl. J. Med. 344:710-719). Data suggests, however, that anatomical repair of the pathway rather than ectopic placement of the graft may be required to obtain complete recovery (Winkler et al., 2000, Prog. Brain Res. 127:233-265). Additionally, fetal nigral transplant therapy requires human fetal tissues from at least 5-10 fetuses in order to have a clinically reliable improvement in the patient, which poses enormous ethical, legal, and safety issues. Thus, there is an urgent need for alternative sources of neuronal cells such as dopaminergic neurons to treat neurodegenerative disorders and neuronal diseases.

Recently, a renewable source of neural stem cells was discovered in the adult human brain. Neural stem cells with the capacity to renew themselves and form all cell types of the brain offer a potentially unlimited supply of dopamine producing brain cells, thus promising an entirely new therapeutic approach to neurodegenerative disorders and neuronal diseases (Eriksson et al., 1998, Nature Medicine 4:1313-1317). It has been reported that cultures of neural stem cells derived from the embryonic human forebrain can be expanded up to ten million fold in vitro. These adult neural stem cells have been transplanted into adult rats that are a well characterized model of Parkinson's disease. The cells in this animal model survived for up to a year after transplantation, differentiated into neurons, and were able to decrease motor disorders in some of the experimental animals (Svendsen et al., 1997, Exp. Neurol. 148:135-146). Unfortunately, adult neural stem cells have a limited life span in tissue culture (Kukekov et al., 1999, Exp. Neurol. 156:333-344).

One viable alternative source of dopamerinergic neurons, and other neurons that may be used to treat various neurodegenerative disorders and neuronal diseases, are pluripotent embryonic stem (ES) cells, in particular human ES cells. ES cells can proliferate indefinitely in an undifferentiated state and are pluripotent, which means they are capable of differentiating into nearly all cell types present in the body. Because ES cells are capable of becoming almost all of the specialized cells of the body, they have the potential to generate replacement cells for a broad array of tissues and organs such as heart, pancreas, nervous tissue, muscle, cartilage, and the like. ES cells can be derived from the inner cell mass (ICM) of a blastocyst, which is a stage of embryo development that occurs prior to implantation. Human ES cells may be derived from a human blastocyst at an early stage of the developing embryo lasting from the $4^{th}$ to $7^{th}$ day after fertilization. ES cells derived from the ICM can be cultured in vitro and under the appropriate conditions proliferate indefinitely.

ES cell lines have been successfully established for a number of species, including mouse (Evans et al., 1981, Nature 292:154-156), rat (Iannaccone et al., 1994, Dev. Biol., 163: 288-292), porcine (Evans et al., 1990, Theriogenology 33:125-128; Notarianni et al., 1990, J. Reprod. Fertil. Suppl. 41:51-6), sheep and goat (Meinecke-Tillmann and Meinecke, 1996, J. Animal Breeding and Genetics 113:413-426; Notarianni et al., 1991, J. Reprod. Fertil. Suppl. 43:255-60), rabbit (Giles et al., 1993, Mol. Reprod. Dev. 36:130-138; Graves et al., 1993, Mol. Reprod. Dev. 36:424-433), mink (Sukoyan et al., Mol. Reprod. Dev. 1992, 33:418-431), hamster (Doetschman et al., 1988, Dev. Biol. 127:224-227), domestic fowl (Pain et al., 1996, Development 122(8):2339-48), primate (U.S. Pat. No. 5,843,780), and human (Thomson et al., 1998, Science 282:1145-1147; Reubinoff et al., 2000, Nature Biotech. 18:399-403). Like other mammalian ES cells, human ES cells differentiate and form tissues of all three germ layers when injected into immunodeficient mice, proving their pluripotency. Published reports show that human ES cells have been maintained in culture for more than a year during which time they retained their pluripotency, self-renewing capacity, and normal karyotype (Thomson et.al., 1995, PNAS 92:7844-7848).

Studies have shown that ES cells can be differentiated into neural progenitor cells (Zhang et al., 2001, Nature Biotech. 19:1129-33; WO 01/88104; U.S. Ser. Nos. 09/872,183, 09/888,309, 10/157,288; WO 03/000868; each specifically incorporated herein by reference). These cells can then be further differentiated into dopaminergic neurons (Rolletschek et al., 2001, Mech. Dev. 105:93-104). An initial step in the differentiation of ES cells can be the formation of embryoid bodies, for example 1 μM of retinoic acid promotes neural differentiation into embryoid bodies (Bain et al., 1995, Dev. Biol. 168:342-357). While retinoic acid can be used to generate neural cells, retinoic acid is a strong teratogen. Several reports have been published on the differentiation of ES cells into dopaminergic neurons by using stromal cell inducing activity (SIDA) (Kawasaki et al., 2000, Neuron 28:1-20), by expressing nuclear receptor related −1 gene (Nurr-1) (Kim et al., 2002, Nature 418:50-56), or by transplanting undifferentiated ES cells directly into the mouse model (Bjorklund et al., 2002, Proc. Natl Acad. Sci. 99:2344-2349). Lee et al. (2000, Nat. Biotechnol. 18:675-79) reported a method for differentiating ES cells into neural progenitor cells and into dopaminergic and serotonergic neurons in vitro. All of these experiments, however, were carried out using mouse ES cells, and the differentiation protocols yielded dopaminergic neurons ranging from 5-50%. About 20% of the mouse ES cells developed into dopaminergic neurons in the study by Lee et al. (WO 01/83715) and 5-50% in the study by Studer et aL. (WO 02/086073). While dopaminergic neurons have also been differentiated from human ES cells, yields of only 5-7% of dopaminergic neurons, as a percentage of total cells in the population, have been obtained (WO 03/000868).

Parkinson's disease is thought to be a particularly suitable clinical target for a cell transplant strategy since it is characterized by the selective and gradual loss of dopaminergic neurons in the substantia nigra of the midbrain. The loss of dopamine-producing neurons within this specific brain site leads to abnormal firing of nerve cells that results in patients being unable to control or direct their movements. But large numbers of dopaminergic neurons are required for cell replacement therapy. Therefore, alternate protocols are needed for deriving dopaminergic neurons from human ES cells more efficiently, which will both accelerate the availability of this treatment for Parkinson's disease and increase the success rate of treatment. Additionally, these dopaminergic neurons can be utilized in vitro to help identify substances that will prevent or reduce death of dopamine producing brain cells in neurodegenerative disorders and neuronal diseases.

BRIEF SUMMARY OF THE INVENTION

The present disclosure relates to improved methods of producing neuroprogenitor cells, as well as terminally differentiated neurons, from pluripotent stem cells such as human embryonic stem cells. For example, the present disclosure demonstrates that a population of human embryonic stem cells can differentiate into a high proportion of neurons positive for tyrosine hydroxylase (TH), a specific marker for dopaminergic neurons (e.g., at least about 60%). The present disclosure also demonstrates that a population of human embryonic stem cells can differentiate into a high proportion of serotonergic neurons. The percentages of dopaminergic and serotonergic neurons generated according to the methods of the present disclosure are higher than previously described methods. The methods disclosed herein may also be used to generate cells with the phenotypic characteristics of cholinergic and sensory neurons, as well as astrocytes and oligodendrocytes, from human embryonic stem cells.

The present disclosure provides a differentiated cell population in an in vitro culture obtained by differentiating primate pluripotent stem cells, wherein at least 60% of the differentiated cells are dopaminergic neurons, express tyrosine hydroxylase, or are dopaminergic neurons which express tyrosine hydroxylase. In other embodiments, at least about 30%, 40%, 50%, 70%, 80%, 90%, 95% or 99% of the differentiated cells are dopaminergic neurons. The present disclosure also provides a differentiated cell population in an in vitro culture obtained by differentiating primate pluripotent stem cells, wherein at least 30% of the differentiated cells are serotonergic neurons. In other embodiments, at least about 40%, 50%, 60%, 70%, 80%, 90%, 95% or 99% of the differentiated cells are serotonergic neurons. In a preferred embodiment, the primate pluripotent stem cells differentiated into neuroprogenitor cells or neurons are human embryonic stem cells.

The present disclosure also provides methods for generating differentiated neural cell populations from primate pluripotent stem cells comprising the following steps:
(a) expanding a culture of primate pluripotent stem cells;
(b) culturing the pluripotent stem cells to select for neuroprogenitor cells that are positive for nestin;
(c) sorting the nestin-positive neuroprogenitor cells for enrichment of NCAM-positive cells;
(d) differentiating the nestin-positive, NCAM-positive cells to generate a differentiated neural cell population by culturing the cells in a differentiation media.

In a preferred embodiment, the primate pluripotent stem cells are human embryonic stem cells. In another preferred embodiment, the pluripotent stem cells used in the above methods are preferably derived using a laser ablation technique.

In other embodiments, the above methods further include the step of culturing the pluripotent stem cells of step (b) to form embryoid bodies. Preferably, these embryoid bodies are cultured under conditions which select for neuroprogenitor cells that are positive for nestin, for example by culturing the pluripotent stem cells or embryoid bodies in serum-free medium. In preferred embodiments, the serum-free medium is ITSFn serum-free defined medium, which preferably includes one or more soluble factors selected from the group consisting of insulin, sodium selenite, basic fibroblast growth factor, transferrin, and fibronectin. In preferred embodiments, these methods will generate neuroprogenitor cells which preferably comprise at least about 60-75% nestin-positive cells, more preferably about 80-90% nestin-positive cells, and most preferably about 95-99% nestin-positive cells.

The nestin-positive neuroprogenitor cells may then be sorted to enrich for NCAM-positive cells using a suitable immunological technique such as immunolabeling and fluorescence sorting, for example Magnetic Cell Sorting (MACS), solid phase adsorption, fluorescence-activated cell sorting (FACS), flow immunocytochemistry for cell-surface markers, or flow cytometry assays. In preferred embodiments, these methods will generate nestin-positive cells which preferably comprise at least about 40-70% NCAM-positive cells, more preferably about 50-60% NCAM-positive cells, and most preferably about 80-99% NCAM-positive cells. In certain embodiments, the above methods further include the step of expanding the nestin-positive, NCAM-positive neuroprogenitor cells of step (c) in expansion medium, preferably for 6-10 days. Preferably, the expansion medium comprises one or more soluble factors selected from the group consisting of insulin, sodium selenite, transferrin, laminin, putrescine, progesterone, basic fibroblast growth factor (bFGF), epidermal growth factor (EGF), sonic hedgehog (SHH), fibroblast growth factor-8 (FGF-8), and brain derived neurotropic factor (BDNF).

The nestin-positive, NCAM-positive neuroprogenitor cells are preferably expanded in culture and serially passed for one or more population doublings. These cells may also be cryopreserved in liquid nitrogen. NCAM-positive neuroprogenitor cells are preferably grown in differentiation media for 30-50 days as set forth in step (d) of the above methods. In preferred embodiments, the differentiation media comprises Neurobasal medium supplemented with fetal calf serum, B27, ascorbic acid, and N-acetyl cysteine. In another preferred embodiment, the differentiation media will include TGF-β3 or interleukin-1β or both. Preferably, the differentiation media further comprises one or more differentiation agents selected from the group consisting of ascorbic acid, N-acetyl, cysteine glial cell line derived neurotropic factor (GDNF), dibutyrl-cyclic AMP (db-cAMP), brain derived neurotropic factor (BDNF), neuturin, sonic hedgehog protein (SHH), and fibroblast growth factor-8 (FGF-8).

In preferred embodiments, the methods disclosed above are used to generate differentiated neural cell populations which preferably comprise about 40-60% dopaminergic neurons, more preferably about 70-80% dopaminergic neurons, and most preferably about 90-99% dopaminergic neurons. In certain embodiments, these methods are used to generate differentiated neural cell populations which preferably comprise about 20-50% serotonergic neurons, more preferably about 30-70% serotonergic neurons, and most preferably about 60-99% serotonergic neurons. In other embodiments, these methods are used to generate differentiated neural cell populations which preferably comprise about 15-40% oligodendrocytes, more preferably about 25-50% oligodendrocytes, and most preferably about 60-99% oligodendrocytes.

The present disclosure provides methods of generating dopaminergic neurons from neuroprogenitor cells, comprising enriching the neuroprogenitor cells for cells that are positive for nestin, and differentiating the nestin-positive cells to generate dopaminergic neurons by culturing the cells in the presence of TGF-β3 or interleukin-1β or both. Preferably, at least about 40-99% of the nestin-positive cells differentiate into dopaminergic neurons using these methods. In other embodiments, these methods further comprise enriching the neuroprogenitor cells for cells that are positive for NCAM, and these nestin-positive, NCAM-positive cells are preferably differentiated to generate dopaminergic neurons (e.g., at least about 60-99% of the cells differentiate into dopaminergic neurons). The present disclosure also provides methods of generating neurons from neuroprogenitor cells, comprising enriching the neuroprogenitor cells for cells that are positive for nestin and NCAM, and differentiating the nestin-positive, NCAM-positive cells to generate serotonergic neurons by culturing the cells in the presence of TGF-β3 or interleukin-1β or both. Preferably, at least about 30-99% of the nestin-positive, NCAM-positive cells differentiate into serotonergic neurons using these methods.

The present disclosure also provides methods for treating subjects with neurodegenerative disorders or neuronal diseases by administering to a subject differentiated neural cells derived from primate pluripotent stem cells as described herein. For example, the differentiated neural cell population may be derived as follows:
 (a) expanding a culture of primate pluripotent stem cells;
 (b) culturing the pluripotent stem cells to select for neuroprogenitor cells that are positive for nestin;
 (c) sorting the nestin-positive neuroprogenitor cells for enrichment of NCAM-positive cells;
 (d) differentiating the nestin-positive, NCAM-positive cells to generate a differentiated neural cell population by culturing the cells in a differentiation media.
 (e) administering a therapeutically effective amount of the differentiated neural cell population into the central nervous system of the subject.

Preferably, the differentiation media includes TGF-β3 or interleukin-1β or both. In preferred embodiments, the subject is a patient, more preferably a human patient, and the primate pluripotent stem cells are human embryonic stem cells. Preferably the human embryonic stem cells are histocompatible with the patient, for example if the pluripotent stem cells used have essentially the same genome as the patient. In certain embodiments, dopaminergic, serotonergic, cholinergic, or sensory neurons, or alternatively astrocytes or oligodendrocytes, are isolated from the differentiated neural cell population and administered to the patient. These cells, including the differentiated neural cell population, can be administered to the subject to treat a variety of neurodegenerative disorders or neuronal diseases, including but not limited to a CNS disorder, Parkinson's disease, Alzheimer's disease, Huntington's disease, spinal cord injury, amyotrophic lateral sclerosis (ALS), epilepsy, stroke, and ischemia. Preferably the cells are administered by transplantation, for example by transplanting the desired cells into the brain of the subject.

In other embodiments, the differentiated neural cells derived from primate pluripotent stem cells as described herein can be used to screen compounds, for example small molecules and drugs, for their effect on the differentiated neural cells or the activity of these cells. The compounds can also be screened for neural cell toxicity or modulation. A compound can be evaluated by adding the compound to a population of differentiated neural cells and comparing the survival, morphology, phenotype, functional activity, or other characteristics of the cells with differentiated neural cells cultured under similar conditions but not exposed to the compound. For example, the compounds can be screened to determine whether they effect changes in neurotransmitter synthesis, release, or uptake by the cells.

BRIEF DESCRIPTION OF THE SEVERAL VIEWS OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 1 shows neuroprogenitor cells derived from human embryonic stem cells that are positive for Nestin: (A) shows neuroprogenitor cells that are immunoreactive with the nestin marker; (B) is a phase contrast photograph of nestin-positive cells that were expanded under serum-free conditions in the presence of selected growth factors.

FIG. 2 shows a FACS analysis of nestin-positive cells derived from human embryonic stem cells and labeled with NCAM-FITC: (A) shows an analysis of the unlabeled cells, which were treated with anti-rabbit FITC; (B) shows an analysis of cells that were treated with a primary antibody for NCAM, and labeled with anti-rabbit FITC (secondary antibody). In this study, about 50-60% of the nestin-positive cells were immunopositive for NCAM.

FIG. 3A and 3B are fluorescent micrographs of NCAM-positive cells derived from human embryonic stem cells that were sorted using MACS and replated on tissue culture plates.

FIG. 4A and 4B are fluorescent micrographs of neurons labeled with MAP-2 and β tubulin derived from human embryonic stem cells.

FIG. 5 shows the presence of neurons positive for tyrosine hydroxylase (TH): (A) immunofluorescence analysis demonstrated that about 60% of the neurons were positive for TH in an enriched population of NCAM-positive cells using MACS; (B) immunofluorescence analysis showed that about 40% of the neurons were positive for TH after the expansion and differentiation of unsorted nestin-positive cells.

FIG. 6 is a representative fluorescence micrograph of oligodendrocytes. Immunoflourescence analysis demonstrated that approximately 25-30% of the isolated nestin-positive cells stained positively as oligodendrocytes.

FIG. 7 is a representative fluorescence micrograph of neuronal cells expressing the neurotransmitter Serotonin. Approximately 30% of nestin-positive cells, as well as approximately 20% of NCAM-positive cells, were immunoreactive with Serotonin.

FIG. 8 is a fluorescent micrograph of dopaminergic neurons immunolabeled for TH (green) and another neuron specific antigens (red): colocalisation of TH with (A) β tubulin; (B) MAP-2; (C) Nurr1; and (D) DAT.

FIG. 9 is a bar graph showing the percentage of MAP-2-positive neurons positive for TH (dopaminergic neurons): as shown, the percentage of neurons positive for TH increases over 7, 22, and 37 days of further differentiation.

FIG. 10 is a bar graph showing a quantitative analysis of different neuronal cell populations in NCAM-positive enriched cells: approximately 60% of the NCAM-positive cells were also immunopositive for TH; approximately 30% were immunopositive for Serotonin; and approximately 15% were immunopositive for GABA and glutamate.

FIG. 11 is a bar graph showing a quantitative analysis of different neuronal cell populations after expansion and differentiation of nestin-positive cells as analyzed by immunoflourescence: approximately 40% of the nestin-positive cells were immunopositive for TH; approximately 30% were immunopositive for Serotonin; approximately 28% were immunopositive for oligodendrocyte, and approximately 2% were immunopositive for glial fibrillar acidic protein (GFAP, a marker for astrocytes).

FIG. 12 shows the gene expression profile of human embryonic stem cells during in vitro terminal-differentiation of these cells under the conditions disclosed in Example 1: UD=undifferentiated; EB=embryoid bodies; NS=nestin-positive cells; NE=nestin expansion cells; and the remaining time points indicate the number of days cells were cultured in Neurobasal medium and selected growth factors as disclosed in Example 1. Transcription of factors specific to dopaminergic neurons such as Nurr1, En-1, D2RL are expressed during early stages of differentiation. Expression of the dopaminergic neuron specific gene TH was observed in all stages except undifferentiated stem cells. The absence of any expression of DBH confirmed the midbrain phenotype of these cells.

FIG. 13 shows the intracellular levels of dopamine in cell lysates as determined by RP-HPLC at 7, 22, and 37 days of differentiation. In the presence of growth factors, dopamine levels were much higher (4-6 μg/ml) than in untreated cells (1-4 μg/ml). No dopamine was detected in cells treated with MPTP at 7 and 22 days, while the level of dopamine was reduced at 37 days.

FIG. 14 is a bar graph demonstrating that KCl causes dopamine release in differentiated cells cultured in conditioned medium after 7, 22, 37 days of differentiation. The cells were stimulated with 56 mM KCl for 15 minutes to induce secretion of dopamine; the culture supernatant was stabilized with 7.5% orthrophosphoric acid and sodium metabisulphite before analysis by RP-HPLC.

DETAILED DESCRIPTION OF THE INVENTION

The present disclosure provides methods for the efficient generation of cells of neural lineage that are differentiated from pluripotent stem cells. The cells generated herein include but are not limited to cells with the phenotypic characteristics of neuroprogenitor cells, dopaminergic, serotonergic, cholinergic, and sensory neurons, as well as astrocytes and oligodendrocytes. Cells generated herein are identified by phenotypic characteristics, morphological characteristics, and/or cell markers, which are readily appreciated by those of skill in the art of evaluating such cells. As used herein, the term "neuroprogenitor cell" is interchangeable with the terms "neural progenitor cell" or "neural precursor cell," and refers to a cell that can generate progeny that are either neuronal cells, such as neuronal precursors or neurons, or glial cells, such as glial precursors, astrocytes, or oligodendrocytes. The methods disclosed herein involve culturing cells in a combination of soluble factors and environmental conditions which encourage the cells to differentiate into cells of neural lineage. In addition, physical separation or manipulation techniques can be used to further enrich for a desired neural cell type.

These precursor and differentiated neural cells can be used for a number of applications, including therapeutic and experimental applications, as well as in vitro drug development and screening, such as screening a compound for neural cell toxicity or the ability to modulate the function of neuronal cells. Generation of precursor and differentiated neural cells such as dopaminergic and serotonergic neurons, as well as other specialized neuronal cell types, from pluripotent stem cells offers a potentially unlimited supply of these neurons, with tremendous potential benefit to individuals suffering from debilitating neurodegenerative disorders and neuronal diseases. The precursor and differentiated neural cells described herein are typically the progeny of the cell population from which they were derived, and therefore will have essentially the same genome as the parent population, including a parent population that has been genetically altered, transformed, or transfected.

One embodiment of the present disclosure is directed to improved methods for generating neurons from pluripotent stem cells, preferably primate embryonic stem (ES) cells or primate embryonic germ (EG) cells, that have characteristics of midbrain neurons, such as dopaminergic neurons. Another embodiment is directed to improved methods for generating neurons from pluripotent stem cells, preferably primate ES cells or primate EG cells, that have characteristics of hindbrain neurons, such as serotonergic neurons. The primate ES cells or EG cells that can be used in these methods are most preferably human ES cells or EG cells. These neurons are derived from pluripotent stem cells by culturing the cells in the presence of certain soluble factors and environmental conditions.

As used herein, the term "dopaminergic neurons" refer to neuronal cells which express tyrosine hydroxylase (TH), the rate-limiting enzyme for dopamine synthesis. Preferably dopaminergic neurons secrete the neurotransmitter dopamine, and have little or no expression of dopamine-β-hydroxylase. Dopaminergic neurons in vivo innervate the striatum, limbic system, and neocortex, and reside in the ventral midbrain together with several other classes of neurons including motor neurons. Dopaminergic neurons are specifically located in the substantia nigra of midbrain, and control postural reflexes, movement, and reward-associated behaviors. The loss of normal functional dopaminergic neurons results in Parkinson's disease, and their abnormal function has been associated with schizophrenia and drug addiction. As used herein, "serotonergic neurons" refer to neurons which secrete the neurotransmitter serotonin (5-hydroxytryptamine). Serotonergic neurons typically have a slow, rhythmic pattern of firing and are concentrated in vivo in the ventral and ventrolateral aspects of the hindbrain and innervate most parts of the central nervous system including the cerebral cortex, limbic system, and spinal cord. These neurons control levels of awareness, arousal, behavior and food intake. The abnormal function of serotonergic neurons has been linked to aggression, depression (including suicidal behavior), and schizophrenia.

The present disclosure is directed to improved methods of differentiating pluripotent stem cells into neuroprogenitor cells, as well as into a differentiated population of neural cells having the phenotypic, molecular, and/or cellular characteristics similar to cells of neural lineage. The pluripotent stem cells can be human ES cells, and the differentiated neural cells can be dopaminergic neurons or serotonergic neurons. The present disclosure also relates to cells and cell populations produced by the disclosed methods. In certain embodiments, the disclosed methods comprise the following steps:

1. A population of pluripotent stem cells are isolated; the pluripotent stem cells are preferably human ES cells derived using a novel laser ablation technique.
2. The pluripotent stem cells are expanded to provide sufficient starting material.
3. The pluripotent stem cells are cultured in suspension to generate embryoid bodies.
4. The embryoid bodies are replated on a substrate and incubated in a serum-free medium which selects for neuroprogenitor cells that are positive for nestin.
5. Nestin-positive cells are sorted to isolate an enriched population of cells positive for NCAM.
6. Nestin-positive and/or NCAM-positive neuroprogenitor cells are expanded in an expansion medium, which comprises soluble factors related to the nervous system.
7. Nestin-positive and/or NCAM-positive neuroprogenitor cells are differentiated into mature neurons in Neurobasal medium, which comprises a combination of soluble factors related to the nervous system.

Sources of Pluripotent Stem Cells

The methods disclosed herein for the differentiation of cells of neural lineage from pluripotent stem cells involve the use of specific culture conditions, which direct differentiation of a remarkably high proportion of pluripotent stem cells into specific neuronal cell types. Pluripotent stem cells are derived from pre-embryonic, embryonic, or fetal tissues any time after fertilization, which, under the appropriate conditions, are able to differentiate into several different cell types that are derivatives of all three germ layers (endoderm, mesoderm, and ectoderm). Cells of neural lineage can also be derived from stem cells isolated from fetal or adult tissue that have the capacity to differentiate or be reprogrammed into cells of neural lineage. Pluripotent stem cells include but are not limited to mammalian ES cell and EG cells, preferably primate or human ES cells and EG cells. Preferably, the undifferentiated pluripotent stem cells have the capacity to divide and proliferate indefinitely in culture. As used herein, the term "differentiation" refers to a process whereby undifferentiated pluripotent stem cells or precursors cells acquire a more specialized fate. For example, a differentiated cell has a phenotype which is characteristic of a particular cell type or tissue.

In a preferred embodiment, the ES cells and ES cell lines used herein are derived from the inner cell mass of a blastocyst. These blastocysts may be isolated from recovered in vivo fertilized preimplantation embryos, or from in vitro fertilization (IVF), for example embryos fertilized by conventional insemination, intracytoplasmic sperm injection, or ooplasm transfer. Human blastocysts are obtained from couples or donors who voluntarily donate their surplus embryos. These embryos are used for research purposes after acquiring written and voluntary consent from these couples or donors. Alternatively, blastocysts may be derived by transfer of a somatic cell or cell nucleus into an enucleated oocyte of human or non-human origin, which is then stimulated to develop to the blastocyst stage. The blastocysts used may also have been cryopreserved, or result from embryos which were cryopreserved at an earlier stage and allowed to continue to develop into a blastocyst stage embryo. The development of both the blastocyst and the inner cell mass will vary according to the species, and are well known to those of skill in the art.

Primate or human ES cells may be derived from a blastocyst using standard immunosurgery techniques as disclosed in U.S. Pat. Nos. 5,843,780 and 6,200,806, Thomson et al. (Science 282:1145-1147, 1998) and Reubinoff et al. (Nature Biotech. 18:399-403, 2000), each specifically incorporated herein by reference. Although ES cells derived in any number of the ways known to one of skill in the art can be used in the disclosed methods, a preferred embodiment uses human ES cells derived by a unique method of laser ablation (U.S. Ser. No. 10/226,711, specifically incorporated herein by reference). In brief, this method isolates cells from the inner cell mass of a blastocyst through laser ablation of part of the zona pellucida and trophectoderm of the blastocyst, which forms an aperture or hole in the blastocyst through which cells of the inner cells mass can be aspirated. These cells can then be further cultured to establish ES cell lines. This technique is advantageous because it allows the isolation of cells of the inner cell mass without undergoing the conventional cumbersome procedure of immunosurgery. In addition, ES cell lines generated using this technique, in particular human ES cell lines, can be isolated in the absence of any animal generated antibodies and sera, which minimizes the risk of any transmission of animal microbes to the ES cell lines. In another embodiment, human EG cells are used that are derived from primordial germ cells present in human fetal material (U.S. Pat. No. 6,090,622, and Shamblott et al., 1998, Proc. Natl. Acad. Sci. USA. 95:13726-13731, each specifically incorporated herein by reference).

Preferably, ES cell lines can be maintained in culture in an undifferentiated state for a prolonged period of time, for example over one year, and maintain a normal euploid karyotype. Human ES cells may be morphologically identified by high nucleus to cytoplasm ratios, prominent nucleoli, and compact colony formation, with often distinct cell borders and colonies that are often flatter than mouse ES cells. Human ES cells are also preferably immunoreactive with markers for human pluripotent ES cells, for example SSEA-3, SSEA-4, GCTM-2 antigen, and TRA 1-60, as described by Thomson et al. (1998), Reubinoff et al. (2000), Buehr and Mclaren (1993), each specifically incorporated herein by reference. Preferably the human ES cells also express alkaline phosphatase, as well as OCT-4. In other embodiments, human ES cells are able to form embryoid bodies under non-adherent culture conditions (U.S. Pat. No. 6,602,711, incorporated herein by reference). These embryoid bodies can be used to derive differentiated derivatives of the endoderm, mesoderm, and ectoderm germ layers, as well as other desired cell lineages.

Pluripotent stem cells, particularly human ES or EG cells, can be propagated continuously under culture conditions that maintain the cells in a substantially undifferentiated state. ES cells must be kept at an appropriate cell density and repeatedly dissociated and subcultured while frequently exchanging the culture medium to prevent them from differentiating. For general techniques relating to cell culture and culturing ES cells, the practitioner can refer to standard textbooks and reviews, for example: E. J. Robertson, "*Teratocarcinomas and embryonic stem cells: A practical approach*" ed., IRL Press Ltd. 1987; Hu and Aunins, 1997, Curr. Opin. Biotechnol. 8(2):148-53; Kitano, 1991, Biotechnology 17:73-106; Spier, 1991, Curr. Opin. Biotechnol. 2:375-79; Birch and Arathoon, 1990, Bioprocess Technol. 10:251-70; Xu et al., 2001, Nat. Biotechnol. 19(10):971-4; and Lebkowski et al., 2001, Cancer J. 7 Suppl. 2:S83-93; each specifically incorporated herein by reference.

Traditionally, ES cells are cultured in ES medium on a layer of feeder cells. Feeder cell layers are cells of one tissue type that are co-cultured with ES cells, and provide an environment in which the ES cells may grow without undergoing substantial differentiation. Methods for culturing ES cells on feeder layers are well known to those of skill in the art (U.S. Pat. Nos. 5,843,780 and 6,200,806, WO 99/20741, U.S. Ser. Nos. 09/530,346 and 09/849,022, WO 01/51616, each specifically incorporated herein by reference). The feeder layer preferably reduces, inhibits, or prevents differentiation of ES cells. Feeder layers are typically an embryonic fibroblast feeder layer of either human or mouse origin, for example mouse embryonic fibroblasts, human embryonic fibroblasts, human fibroblast-like cells or mesenchymal cells derived from human embryonic stem cells, or STO cells.

ES cells are preferably cultured in the presence of ES medium, which reduces, inhibits, or prevents the differentiation of the ES cells. Preferably, ES medium used to culture ES cells is supplemented with a nutrient serum, for example a serum or serum-based solution that supplies nutrients effective for maintaining the growth and viability of ES cells. The nutrient serum may be animal serum such as fetal bovine serum (FBS) or fetal calf serum (FCS) (U.S. Pat. Nos. 5,453,357, 5,670,372, and 5,690,296, incorporated herein by reference). The ES medium may also be serum-free (WO 98/30679, WO 01/66697, U.S. Ser. No. 09/522,030, each specifically incorporated herein by reference). An example of suitable ES medium with serum for culturing ES cells is Dulbecco's modified Eagle's medium (DMEM), without sodium pyruvate, with high glucose content (70-90%) (GIBCO), supplemented with FBS or FCS (10-30%), β-mercaptoethanol (0.1 mM), non-essential amino acids (1%), and L-Glutamine 2 mM, 4 ng/ml basic fibroblast growth factor (bFGF), 50 U/ml penicillin, 50 µg/ml streptomycin, and 1000 U/ml of Leukemia inhibitory factor (LIF). An example of suitable serum-free ES medium for culturing ES cells is 80% "KnockOut" Dulbecco's modified Eagle's medium (DMEM) (GIBCO), 20% KnockOut SR (a serum-free replacement, GIBCO), β-mercaptoethanol (0.1 mM), non-essential amino acids (1%), and L-Glutamine 1 mM.

ES cells may also be cultured under feeder-free culture conditions. Methods for culturing ES cells in a feeder-free culture are well known to those of skill in the art (U.S. Publ. No. 2002/0022268, WO 03/020920, U.S. Ser. No. 10/235,094, each specifically incorporated herein by reference). ES cells in a feeder-free culture are preferably grown on a suitable culture substrate, for example an extracellular matrix, such as Matrigel® (Becton Dickenson) or laminin. Feeder-free cultures also preferably use conditioned medium to support the growth of ES cells. Conditioned medium is prepared by culturing a first population of either murine embryonic fibroblasts or human embryonic fibroblast cells in a medium for a sufficient period of time to produce "conditioned" medium which will support the culturing of ES cells without substantial differentiation. Alternatively, the feeder-free culture can combine an extracellular matrix with an effective medium that is added fresh to the culture without being conditioned by another cell type (U.S. Publ. No. 2003/0017589, specifically incorporated herein by reference).

Preparation of Neuroprogenitor Cells

Isolated pluripotent stem cells may be expanded and then subjected to culture conditions which causes them to differentiate into neuroprogenitor cells. For pluripotent stem cells to advance along the neural differentiation pathway, the cells are cultured according to differentiation protocols disclosed herein. The pluripotent stem cells are cultured on a suitable substrate in a differentiation nutrient medium which contains differentiation agents such as soluble factors and growth factors. Suitable substrates include but are not limited to solid surfaces coated with a positive-charge, for example poly-L-lysine or polyornithine, substrates coated with extracellular matrix components, for example fibronectin, laminin, or Matrigel®, or a combination thereof. Preferred differentiation nutrient mediums are those that support the proliferation, differentiation, and survival of desired neural cell types, and may include one or more suitable differentiation agents. As used herein, the term "growth factor" refers to proteins that bind to receptors on the cell surface with the primary result of activating cellular proliferation and differentiation. Suitable soluble factors include but are not limited to neurotrophins, mitogens, stem cell factors, growth factors, differentiation factors (e.g., TGF-β Superfamily), TGF-β Superfamily agonists, neurotrophic factors, antioxidants, neurotransmitters, and survival factors. Many soluble factors are quite versatile, stimulating cellular division in numerous different cell types, while others are specific to particular cell types.

Suitable differentiation agents that specifically encourage the differentiation of neuronal cell types include but are not limited to progesterone, putrescine, laminin, insulin, sodium selenite, transferrin, neurturin, sonic hedgehog (SHH), noggin, follistatin, epidermal growth factor (EGF), any type of fibroblast growth factor (for example FGF-4, FGF-8, basic fibroblast growth factor (bFGF)), growth and differentiation factor 5 (GDF-5), members of the neurotrophin family (nerve growth factor (NGF), neurotrophin 3 (NT-3), neurotrophin 4 (NT-4), brain derived neurotropic factor (BDNF)), transforming growth factor α (TGF-α), transforming growth factor beta-3 (TGF β3), platelet-derived growth factor (PDGF-AA), insulin-like growth factor (IGF-1), bone morphogenic proteins (BMP-2, BMP-4), glial cell derived neurotrophic factor (GDNF), retinoic acid (RA), midkine, ascorbic acid, dibutyryl cAMP, dopamine, and ligands to receptors that complex with gp130 (e.g., LIF, CNTF, SCF, IL-11, and IL-6). Differentiation nutrient mediums may also contain additives that help sustain cultures of neural cells, for example N2 and B27 additives (Gibco).

Pluripotent stem cells are first induced to form embryoid bodies. Embryoid bodies are plated directly onto a suitable substrate with or without an extracellular matrix component such as fibronectin or laminin, and cultured in a suitable differentiation nutrient medium adapted to promote differentiation into neuroprogenitor cells, such as nestin-positive neuroprogenitor cells. Nestin is a cell marker characteristic of neural precursors cells. In another embodiment, the pluripotent stem cells are first aggregated into a heterogeneous cell population by forming embryoid bodies, for example by culturing the pluripotent stem cells in suspension. These cells can be cultured in nutrient medium with or without serum, as well as with one or more of the differentiation agents listed above, to promote differentiation of cells in the embryoid bodies. As used herein, the term "embryoid bodies" refer to an aggregation of differentiated cells generated when pluripotent stem cells are grown in suspension culture, or overgrow in monolayer cultures. Embryoid bodies may also have undifferentiated cells in the aggregation of cells. Preferably this aggregation of cells is surrounded by primitive endoderm. Embryoid bodies typically contain cells derived from all three germ layers, ectoderm, mesoderm and endoderm. In mature human embryoid bodies, it is possible to discern cells bearing markers of various cell types, such as neuronal cells, haematopoietic cells, liver cells, and cardiac muscle cells. Some cells in mature embryoid bodies can behave functionally like differentiated cells. For example, active cardiac muscle cells can cause an embryoid body to pulsate. Preferably the differentiation of pluripotent stem cells is controlled so that specific cell types can be obtained for therapeutic purposes.

The embryoid bodies are cultured until they reach sufficient size or desired differentiation, for example after 3-10 days of culture, and then plated onto a substrate. Preferably the substrate is coated with extracellular matrix components, including but not limited to poly-1-lysine, poly-1-ornithine, laminin, collagen, fibronectin, Matrigel®, or combinations thereof. Preferably the embryoid bodies are plated directly onto the substrate without dispersing the cells. The embryoid bodies are then cultured under conditions to encourage further differentiation of the plated cells, for example in ITSFn (nestin selection) serum-free defined medium which is selective for nestin-positive cells. Nestin is an intermediate filament protein expressed in the neuroepithelium. Preferably, the cells are selected for nestin-positive cells over a period of 5-16 days. Preferably, the ITSFn medium used for expansion of nestin-positive cells is DMEM:F-12 supplemented with one or more growth factors selected from the group consisting of progesterone, putrescine, laminin, insulin, sodium selenite, transferrin, bFGF, SHH, EGF, FGF-2, FGF-8, and BDNF.

This heterogeneous cell population which includes nestin-positive cells is subsequently expanded or sorted for enrichment of neural cell adhesion molecule (NCAM) positive cells. NCAM is a surface marker characteristic of neural cells. NCAM-positive cells can be sorted immediately after nestin-positive cells are selected for, or after the nestin-positive cells are expanded in culture. In certain embodiments, the cells are sorted for NCAM-positive cells by contacting the cells with an antibody or ligand that binds to NCAM, followed by the separation of the specifically recognized cells using a suitable immunological technique such as immunolabeling and fluorescence sorting, for example solid phase adsorption, fluorescence-activated cell sorting (FACS), flow immunocytochemistry for cell-surface markers, flow cytometry assays, or magnetic cell sorting (MACS). Other methods for isolating NCAM-positive cells, including but not limited to differential plating, immune-specific lysis of contaminating cells, or harvesting techniques are well known to those of skill in the art. In preferred embodiments, sorting the nestin-positive cells, for example by MACS, enriches the population of viable nestin-positive cells expressing NCAM to about 40-70%, preferably to about 60%-80%, more preferably to about 85%-90%, and most preferably to about 95%-99%.

In one embodiment, the embryoid bodies are generated from human ES cells by culturing the cells on a bacteriological plate in the absence of feeder cells in an appropriate media. Preferably the human ES cells are dissociated into clusters and then plated in non-adherent plates to facilitate the development of embryoid bodies. The appropriate media preferably contains DMEM with high glucose and is supplemented with 10-20% FCS. Other supplements may also be added to the media, such as 0.1 mM 2-mercaptoethanol, 2 mM L-glutamine, 50 U/ml of penicillin, and 50 µg/ml of streptomycin. The embryoid bodies are preferably allowed to grow for 4-8 days, and then the embryoid bodies are replated on a culture plate coated with 0.1% gelatin in ITSFn serum-free medium for selection of nestin-positive cells. Preferably the ITSFn serum-free medium contains the basal medium DMEM: F-12 (1:1) or IMDM medium, supplemented with the growth factors insulin, sodium selenite, transferrin, and fibronectin, which selects for nestin-positive cells.

In a preferred embodiment, the nestin-positive cells are sorted by MACS to isolate NCAM-positive cells. The NCAM-positive cells are subsequently expanded in medium which helps to increase the percentage of neuroprogenitor cells and further induces these cells to adopt more differentiated phenotypes. Preferably, the NCAM-positive cells are cultured on a substrate which is precoated with extracellular matrix components such as poly-1-lysine, poly-1-ornithine, laminin, collagen, fibronectin, Matrigel®, or combinations thereof. Precoating of culture dishes with an extracellular matrix permits better adhesion and proliferation in the expansion media, as well as gives better results for dopaminergic neuron differentiation. The cells are cultured in an expansion medium, for example DMEM/F12 medium, supplemented with one or more growth factors selected from group consisting of progesterone, putrescine, laminin, insulin, sodium selenite, transferrin, bFGF, SHH, EGF, FGF-2, FGF-8, BDNF, PDGF, IGF-1, CTNF, and NT-3. Although not wishing to be bound by any particular mechanism, it is believed that these various factors present in the expansion medium contribute to the overall increase in the percentage of neuronal cells and further induce midbrain neuronal precursor cells to adopt the dopaminergic phenotype. In preferred embodiments, the nestin-positive NCAM-positive precursor cells are allowed to proliferate for 3-10 days. These cells can also be serially passaged for at least thirty population doublings and frozen for further use without any loss of differentiation potential.

Differentiation of Dopaminergic and Serotonergic Neurons

The neuroprogenitor cells prepared according to the methods disclosed herein can be further differentiated into high proportions of mature neurons, for example dopaminergic neurons and serotonergic neurons. The neuroprogenitor cells can also be further differentiated into astrocytes and oligodendrocytes. Preferably, the nestin-positive and/or NCAM-positive neuroprogenitor cells are expanded from 5-60 days in a Neurobasal medium which facilitates the differentiation of the progenitor cells into terminally differentiated neural cells or mature neurons. In a preferred embodiment, the Neurobasal medium (Gibco) is supplemented with 10% FBS or FCS, B27, and one or more growth factors selected from the group consisting of Interleukin-1β, dibutyrl cyclic AMP (db-cAMP), glial cell derived neurotrophic factor (GDNF), transforming growth factor beta 3 (TGF-β3), transforming growth factor α (TGFα), neurturin, SHH, ascorbic acid, BDNF, FGF-2, FGF-8, N-acetyl cysteine, c-kit ligand, retinoic acid, NT-3, BMP-2, and BMP-4. In a preferred embodiment, the neurobasal medium includes one or more of the following factors: Interleukin-1β, db-cAMP, GDNF, TGF-β3, neurturin, SHH, ascorbic acid, BDNF, FGF-8, and N-acetyl cysteine. In addition, differentiation may be facilitate by withdrawing some or all of the factors that promoted the differentiation, proliferation, or both of the neuroprogenitor cells.

Preferably, a high percentage of the neuroprogenitor cells differentiate into dopaminergic neurons, serotonergic neurons, or oligodendrocytes, for example at least about 20%, 25%, 30%, 35%, 40%, 45%, 50%, 55%, 60%, 65%, 70%, 75%, 80%, 85%, 90%, 95%, or 99% of the cells. In addition, one neural cell type, for example dopaminergic neurons, may be further purified from a population of differentiated neural cells by methods well known to those of skill in the art, such as immunolabeling and fluorescence sorting, for example solid phase adsorption, FACS, MACS, and the like. In one preferred embodiment, the immunosorted enriched population of NCAM-positive cells are expanded and differentiated in appropriate media giving rise to a high percentage (about 60%) of dopaminergic neurons.

Uses for Neuroprogenitor Cells and Differentiated Neural Cells

The neuroprogenitor cells and differentiated neural cells described herein (e.g., mature neurons, astrocytes, and oligodendrocytes) can be utilized for various applications, such as therapeutic applications, as well as for in vitro assessment and screening of various compounds such as small molecule drugs for their effects on these cells. These cells can also be used to prepare cDNA expression libraries to analyze the expression patterns of these cells, as well as to prepare monoclonal or polyclonal antibodies that are specific to markers for the particular cells used, using techniques that are well known to those of skill in the art. These cells can also be use therapeutically to the benefit of individuals suffering from debilitating neurodegenerative disorders and neuronal diseases.

The present disclosure provides for the use of the neuroprogenitor cells and differentiated neural cells described herein to restore central nervous system (CNS) function in a subject in need of such therapy. For example, these cells could be used therapeutically by transplanting them directly into parenchymal or intrathecal sites of the CNS, depending on the disease or condition being treated. These cells may be used to treat acute or chronic damage to the nervous system, as well as debilitating neurodegenerative disorders and neuronal diseases, such as Parkinson's disease, Alzheimer's disease, Huntington's disease, spinal cord injury, amyotrophic lateral sclerosis (ALS), epilepsy, stroke, ischemia, and the like.

One embodiment of the present disclosure relates to methods of treating neurodegenerative disorders or neuronal diseases characterized by the degeneration or destruction of dopaminergic neurons by administration or transplantation of a therapeutically effective amount of dopaminergic neurons derived from pluripotent stem cells, preferably human pluripotent stem cells. In another embodiment, the present disclosure relates to methods of treating neurodegenerative disorders or neuronal diseases characterized by the degeneration or destruction of serotonergic neurons by transplantation of a therapeutically effective amount of serotonergic neurons derived from pluripotent stem cells, preferably human pluripotent stem cells. Preferably, a human patient suffering from a neurodegenerative disorder or neuronal disease is treated by engrafting a therapeutically effective amount of neuroprogenitor cells and differentiated neural cells of the present disclosure into the patient. As used herein, a "therapeutically effective amount" of cells is an amount sufficient to arrest or ameliorate the physiological effects in a subject caused by the loss, damage, or degeneration of differentiated neural cells, such as mature neurons (e.g., dopaminergic and serotonergic neurons), astrocytes, and oligodendrocytes.

The therapeutically effective amount of cells used will depend on the needs of the subject, the subject's age, physiological condition, and health, the desired therapeutic effect, the size of the area of tissue that is to be targeted for therapy, the extent of pathology, and the chosen route of delivery. For example, treatment of a disorder affecting a larger region of the brain could require a larger number of cells to achieve a therapeutic effect when compared to a smaller target region. Cells may also be administered to more than one site in a given target tissue, with multiple small grafts of low cell doses. The cells of the present disclosure may be completely dissociated before transplantation, such as to create a suspension of single cells, or nearly completely dissociated before transplantation, such as to create small aggregates of cells. The cells may be administered in a manner that allows them to graft or migrate to the intended tissue site and reconstitute or regenerate a functionally deficient area.

A suitable range of cells that can be administered to achieve a therapeutically effective can be from about 100 to about 1,000,000 neurons, preferably from about 500 to about 500,000 neurons, or from about 1000 neurons to about 100,000 neurons. Therapeutic concentrations of neural cells administered to a subject can also range from about 10, 100, 500, 1000, 5000, 10,000, 15,000, 20,000, 25,000, 30,000, 35,000, 40,000, 45,000, 50,000, 60,000, 70,000, 80,000, 90,000, 100,000, 150,000, 200,000, 250,000, 300,000, 350,000, 400,000, 450,000 to about 500,000 cells per microliter of a pharmaceutically acceptable carrier. Ranges of concentrations of cells in a carrier include, for example, 100-50,000 cells/μl, 1000-10,000 cells/μl, 5000-25,000 cells/μl, 15,000-45,000 cells/μl, 20,000-50,000 cells/μl, 55,000-200,000 cells/μl, 100,000-40,000 cells/μl, 150,000-50,000 cells/μl, etc. The number of cells grafted into a transplant site will also affect therapeutic efficacy.

For therapeutic applications, it is often preferable that populations of precursors or differentiated neural cells are substantially pure of any undifferentiated pluripotent stem cells. One strategy for removing pluripotent stem cells from a therapeutic preparation is to transfect the cells with a vector that has a gene which is preferentially expressed in undifferentiated cells, the expression of which selects against the pluripotent stem cells. Suitable promoters that are preferentially expressed in undifferentiated cells are the telomerase reverse transcriptase (TERT) promoter and the OCT-4 promoter. The gene expressed in the vector may for example be lytic to the cell, such as a toxin, or it may be selected against by the application of an external agent.

The ability to generate dopaminergic neurons and serotonergic neurons from pluripotent stem cells as disclosed herein is of great clinical relevance for transplantation therapy for a variety of neurodegenerative disorders and neuronal diseases. For example, dopaminergic neurons can be used to treat neurodegenerative disorders and neuronal diseases which are characterized by abnormalities in the regulation of postural reflexes, movement, and reward-associated behaviors, for example Parkinson's disease, schizophrenia, and drug addiction, as well as lesions due to trauma or other illnesses that result in Parkinson-like conditions such as resting tremor, rigidity, akinesia, and postural abnormalities such as akinesia, adipsia, aphagia and sensory neglect. Additionally, serotonergic neurons can be used to treat neurodegenerative disorders and neuronal diseases which are characterized by abnormalities in the regulation of food intake, hormone secretion, stress response, pain and immune function, sexual activity, cardiovascular function, and temperature regulation, for example various psychiatric, neurologic, and other diseases, e.g., mental depression, proclivity to suicide, violent aggressive behavior, obsessive-compulsive behavior and anorexia/bulimia, and schizophrenia.

In another embodiment, the present disclosure relates to the coadministration of one or more neuronal survival factors with neuroprogenitor cells and differentiated neural cells of the present disclosure derived from pluripotent stem cells to treat a neurodegenerative disorder or neuronal disease. The neuronal survival factor(s) may be administered prior to, in conjunction with, in combination with, or after the administration of the desired cells. As used herein, a "neuronal survival factor" is any substance which causes neurons (either in vitro or in vivo) that are contacted with the factor to survive for a period of time greater than would occur without the presence of the factor. Neuronal survival factors that may be used in the present therapeutic embodiment include but are not limited to Glial-derived neurotrophic factor (GDNF), nerve growth factor (NGF), ciliary neurotrophic factor (CNTF), brain derived neurotrophic factor (BDNF), neurotrophin-3 (NT-3), neurotrophin-4 (NT-4), FGF, IL-1β, TNFα, insulin-like growth factor (IGF-1, IGF-2), and transforming growth factor beta (TGF-β, TGF-β1).

GDNF is known to have trophic activity for embryonic midbrain ventral mesencephalic dopaminergic neurons in vitro (Lin et al., 1993, Science 260:1130-1132; Lin et al., 1994, J. Neurochem. 63:758-768). Recombinant human GDNF has also been demonstrated to induce sprouting of dopaminergic fibers in vivo (Hudson et al., 1993, Soc. Neurosci. Absir. 19:652), increase dopamine turnover in the substantia nigra of rats (Miller et al., 1994, Soc. Neitrosci. Abstr. 20:535-7), protect neurons against 6-OHDA lesions, and augment growth and fiber formation of rat fetal transplants of nigral tissue in oculo (Stromberg et al., 1993, Exp. Neurol. 124:401-412). BDNF is a trophic factor for peripheral sensory neurons, dopaminergic neurons, and retinal ganglia (Henderson et al., 1993, Restor. Neurol. Neurosci. 5:15-28), and has been shown to prevent normally-occurring cell death both in vitro and in vivo (Hofer and Barde, 1988, Nature 331:161-262).

As used herein, the terms "treatment" or "to treat" refer to both therapeutic treatment and prophylactic or preventative measures. Therefore, those in need of treatment include those already with the neurodegenerative disorder or neuronal disease, as well as those in which the neurodegenerative disorder or neuronal disease is to be prevented. The methods of the present disclosure can be used to treat any mammal in need of treatment, including but not limited to humans, primates, and domestic, farm, pet, or sports animals, such as dogs, horses, cats, sheep, pigs, cattle, etc. A "disorder" is any condition that would benefit from treatment with neuroprogenitor cells, differentiated neural cells, or both types of cells of the present disclosure. Examples of disorders that would benefit from implantation of dopaminergic neurons are those associated with improper postural reflexes, movement, and reward-associated behaviors, such as Parkinson's disease, schizophrenia, and drug addiction. Examples of disorders that would benefit from implantation of serotonergic neurons are those characterized by abnormalities in awareness, arousal, behavior, and food intake, including but not limited to aggression, depression (including suicidal behavior), schizophrenia, and anorexia/bulimia. Other disorders that may also benefit from treatment with cells of the present disclosure are Alzheimer's disease, Huntington's disease, and Hirschsprung's disease.

The methods of present disclosure may be advantageously carried out by direct transplantation of neuroprogenitor cells or differentiated neural cells of the present disclosure to the lesioned area. Methods of neuronal transplantation and cell culture are well known to those of skill in the art, e.g., U.S. Pat. No. 5,514,552; Yurek and Sladek, 1990, Annu. Rev. Neurosci. 13:415-440; Rosenthal, 1998, Neuron 20:169-172; Vescovi et al., 1999, J. Neurotrauma 16(8):689-93; Vescovi et al., 1999, Exp. Neuro. 156(1):71-83; Brustle et al., 1999, Science 285:754-56; each specifically incorporated herein by reference. In one embodiment, the dopaminergic neurons of the present disclosure may be implanted in the substantia nigra or striatum of a patient suffering from Parkinson's disease. The cells may be delivered alone or in combination with other factors, for example a neuronal survival factor, and may be delivered along with a pharmaceutically acceptable vehicle. Ideally, such a vehicle would enhance the stability and delivery properties of the cells.

The present disclosure also provides for pharmaceutical compositions containing the cells which can be administered using a suitable vehicle such as liposomes, microparticles, or microcapsules. Cells of the present disclosure may also be supplied in the form of a pharmaceutical composition comprising an isotonic excipient, and prepared under conditions that are sufficiently sterile for human administration. General principles of medicinal formulations of cell compositions is found in *Cell Therapy: Stem Cell Transplantation, Gene Therapy, and Cellular Immunotherapy*, G. Morstyn & W. Sheridan eds, Cambrigge University Press, 1996, and *Hematopoietic Stem Cell Therapy*, E. Ball, J. Lister & P. Law, Churchill Livingstone, 2000, specifically incorporated herein by reference. Additionally, it may be desirable to administer a pharmaceutical composition containing a neuronal survival factor locally to the area in need of treatment, which may be achieved by, for example, local infusion during surgery, injection, a catheter means, or implant means, wherein such implant can be of a porous, non-porous, or gelatinous material, including membranes, such as silastic membranes or fibers.

The neuroprogenitor cells and differentiated neural cells of the present disclosure may be transplanted into a subject as either a substantially homogenous, nearly homogeneous, or heterogeneous cell population. A substantially homogenous cell population comprises greater than 75% of a single cell type, such as a dopaminergic or serotonergic neuron, more preferably greater than 90%, and most preferably greater than 95%-99%. A heterogeneous cell population will consist of two or more cell types mixed in a single cell population, for example dopaminergic neurons, serotonergic neurons, Schwann cells, oligodendrocytes, astrocytes, GABA neurons, and glial cells. The cells may also be genetically altered by methods well known to those of skill in the art to express or release trophic factors, growth factors, neuronal survival factors, or other therapeutic compounds in the damaged area of the brain, central nervous system, peripheral nervous system, or other tissues. The use of promoter and cell type combinations for protein expression is generally known to those of skill in the art of molecular biology, for example, see Sambrook, et al. 1989, Molecular Cloning: A Laboratory Manual $2^{nd}$ Ed. Cold Spring Harbor Laboratory Press, Cold Spring Harbor, N.Y., specifically incorporated herein by reference.

To achieve expression of trophic factors, growth factors, neuronal survival factors, or other therapeutic compounds in the neuroprogenitor cells and differentiated neural cells of the present disclosure, suitable regulatory elements can be derived from a variety of sources, and may be readily selected by one of ordinary skill in the art. Examples of regulatory elements include a transcriptional promoter, enhancer, and RNA polymerase binding sequence, as well as a ribosomal binding sequence, including a translation initiation signal. Other additional genetic elements, such as selectable markers, may also be incorporated into the recombinant molecule. The recombinant molecule may be introduced into the pluripotent stem cells, or the neuroprogenitor cells or differentiated neural cells derived from the pluripotent stem cells, using in vitro delivery vehicles or in vivo techniques. Examples of delivery techniques include retroviral vectors, adenoviral vectors, DNA virus vectors, liposomes, physical techniques such as microinjection, and transfection via electroporation or calcium phosphate precipitation, or other methods known in the art for transfer of creating recombinant cells. The genetically altered cells may be encapsulated in microspheres and implanted into or in proximity to the diseased or damaged tissue. Protocols employed are well-known to those skilled in the art, and may be found, for example, in Ausubel et al., Current Protocols in Molecular Biology, John Wiley & Sons, New York, N.Y., 1997, incorporated herein by reference.

Clinical experiments involving neural transplantation in patients afflicted with Parkinson's disease evolved from basic scientific research using various animal models of parkinsonism as recipients of either fetal embryonic nerve cell or paraneuronal tissue grafts to brain-damaged areas. Animal experimentation with fetal dopaminergic nerve cell grafts have provided encouragement that such grafts could reverse dopaminergic deficits and restore motor function in animals with experimental lesions of the nigrostriatal dopaminergic system. For example, murine mesencephalic cells taken from 14-16 day old embryos have been advantageously employed over those taken from later gestating donors in transplants as homografts or heterografts without immunosuppressive treatment (Yurek and Sladek, 1990, Annu. Rev. Neurosci. 13:415-440). Interestingly, these ages corresponds to the gestational age at which dopaminergic neurons undergo their final cell division (Lauder and Bloom, 1974, J. Comp. Neurol. 155:469-82). Solid grafts of embryonic mesencephalic tissue can also be dissociated into cell suspensions for transplantation. Typical survival rates of such suspensions, however, have been limited to about 10% of the grafted dopaminergic cells (Brudin et al., 1987, Ann. N.Y. Acad. Sci. 495:473-96). Since embryonic mesencephalic tissue is not a pure source of dopaminergic cells—only about 0.1-1.0% of the total viable cells are surviving dopaminergic cells—any graft of dissociated mesencephalic cells preferably contains a minimum of 100,000 to 150,000 viable cells in order to effectively compensate for dopaminergic loss.

Preferably, the cell transplant therapy of the present disclosure also incorporates some means of storing and preserving the neuroprogenitor cells and differentiated neural cells for use in transplant surgery, for example long-term storage by cryopreservation, or short term storage in preservation medium. Cryopreserved embryonic mesencephalic tissue has been successfully stored for up to 70 days and transplanted as homografts in rodent (Collier et al., Progress in Brain Research, Vol. 78, New York, Elsevier (1988), pp. 631-36, specifically incorporated herein by reference) and primate (Collier et al., 1987, Brain Res. 436:363-66, specifically incorporated herein by reference). It has also been demonstrated that embryonic mesencephalic cells can be successfully cultured after cryopreservation. Mesencephalic tissue can also be stored short-term (2-5 days) in preservation medium at 4° C. and subsequently transplanted with surviving graft volumes similar to those for fresh tissue (Sauer et al., 1989, Restor. Neurol. Neurosci. (Suppl.:3.sup.rd Int. Symp. Neural Tranplan.):56, specifically incorporated herein by reference).

Graft placement, and the extent to which the graft reinnervates the striatum, are both important factors for the functional recovery of the mesostriatal dopaminergic system. In the unilaterally dopaminergic-denervated animal, cortically placed dopaminergic grafts have been shown to reduce motor asymmetry, but have little effect on sensory neglect (Bjorklund et al., 1980, Brain Res. 199:307-33; Dunnett et al., 1981, Brain Res. 215:147-61). In contrast, nigral grafts placed in proximity to lateral striatum in bilaterally dopaminergic-denervated animals effectively restored sensory damage (Dunnett et al., 1983, Acta Physiol. Scan. Suppl. 522:39-47). Furthermore, the reversal of akinesia in bilaterally lesioned animals is observed only when the nucleus accumbens is reinnervated by the dopaminergic graft (Nadaud et al., 1984, Brain Res. 304:137-41).

While the transplantation site for dopaminergic graft has most often been in proximity to the ventricular region because of the favorable cerebrospinal fluid (CSF) environment in those regions to provide for graft survival, the degree of dopaminergic degeneration in Parkinson's disease is more pronounced in the putamen than in the caudate nucleus. Dopamine levels in the putamen are often 10-15% lower than in the caudate nucleus (Bemhiemer et al., J. Neurol. Sci. 20:415-55; Nyberg et al., 1983, Neurochem. Pathol. 1: 93-202). Additionally, the caudal putamen is more severely depleted of dopaminergic-neurons than the rostral putamen (Kish et al., 1986, Ann. Neurol. 20:26-31). Of the two striatal components (caudate nucleus and putamen), the putamen receives the majority of motor input via a cortical-thalamic-putamen pathway (DeLong & Georgopoulos, 1983, Handbook of Physiology, Section I: The Nervous System, Vol. 2, ed. Brookhard, Mountcastle, Geiger, pp. 1017-61, Bethesda, Md.: Am. Physiol. Soc.). Therefore, the putamen may be a more favorable site for dopaminergic grafts targeting motor disorders associated with Parkinson's disease.

The neuroprogenitor cells and differentiated neural cells described herein can also be used to screen compounds such as pharmaceutical compounds, solvents, small molecules, peptides, or polynucleotides, as well as for environmental factors such as culture conditions or manipulations, that affect the phenotype or characteristics of these cells. In addition, these cells can be used to assess candidate growth factors or differentiation factors. For example, a candidate pharmaceutical compound can be added to neuroprogenitor cells or mature neurons, either alone or in combination with other drugs, and any changes in the morphology, phenotype, or functional activity in the cells can be assessed and evaluated.

In addition, the neuroprogenitor cells and differentiated neural cells described herein may be further modified at any stage of differentiation. For example, these cells may be genetically modified to have single or multiple genetic modifications, either in a transient or stable fashion. Genetic alterations of these cells may be desirable for many reasons, such as to provide modified cells for gene therapy or replacement tissues for grafting or implantation. The cells of the present disclosure can be genetically modified through the introduction of vectors expressing a selectable marker under the control of a neural-specific promoter, which are well known to those of skill in the art. These cells may also be modified at any stage to express certain markers or genes that can be used to further purify differentiated cells derived from pluripotent stem cells, or alternatively to induce differentiation into particular cell lineages. These cells can be modified to reduce or prevent immune rejection after transplantation, i.e. histocompatibility with the intended recipient.

To increase the replicative capacity of cells generated using the present disclosure, these cells may be telomerized by genetically altering them with a suitable vector so that they express the telomerase catalytic component (TERT). The TERT sequence used may be derived from human or mouse (WO 98/14592 and WO 99/27113, specifically incorporated herein by reference), as well as other mammalian species. Alternatively, transcription of the endogenous TERT gene can be increased. Methods used to genetically modify cells are well known to those of skill in the art. These methods utilize various molecular biology techniques, many of which are generally described in Sambrook, et al. 1989, Molecular Cloning: A Laboratory Manual $2^{nd}$ Ed. Cold Spring Harbor Laboratory Press, Cold Spring Harbor, N.Y., specifically incorporated herein by reference.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

In the following example, applicants of the present disclosure demonstrate the derivation of functional dopaminergic and serotonergic neurons from human embryonic stem cells.

1) Human Embryonic Stem Cells:

To begin, human ES cells were isolated from the inner cell mass of a human blastocyst. The human pluripotent ES cells were derived from excess human blastocysts after obtaining consent from individual patients for the experimental use of the blastocysts. The human ES cell line used herein was derived from cells of the inner cell mass of a human blastocyst using a novel laser ablation technique as disclosed in U.S. Ser. No. 10/226,711, incorporated herein by reference. Briefly, a human blastocyst having a zona pellucida, a trophectoderm, and an inner cell mass was isolated, and an 1.48 μm non-contact diode laser was used to create an aperture through the zona pellucida and the trophectoderm of the human blastocyst. Next, cells of the inner cell mass were isolated by aspiration using an aspiration pipette introduced through the aperture. These cells were subsequently cultured on a 0.1% gelatinized plate with mitomycin-C treated mouse feeder cells in an ES medium, and inner cell mass-derived cell masses were formed. The ES cell medium consisted of Dulbecco's modified Eagles medium (DMEM) or knockout DMEM (Gibco), supplemented with 10-20% ES cell qualified fetal calf serum (FCS) (Hyclone) or serum replacement knockout serum (Gibco), 1% MEM non-essential amino acid solution, 2 mM L-glutamine, 0.1 mM β-mercaptoethanol, 4 ηg/ml basic fibroblast growth factor (bFGF) (Sigma), 50 U/ml penicillin, and 50 µg/ml streptomycin. These inner cell mass-derived cell masses were dissociated, replated on a mouse feeder layer in ES medium, and used to derive human ES cell lines.

Morphologically the human ES cells derived have a high nuclear/cytoplasmic ratio, and were characterized with cell surface markers such as SSEA-1, SSEA-3, SSEA-4, TPA-1-60, TRA-1-81, OCT-4, alkaline phosphatase, telomerase, karyotyping, CD-30, cripto-1, GCNF, c-kit and CD-90.

2) Culture and Expansion of Human Embryonic Stem Cells:

The human ES cells were cultured and proliferated under standard growth conditions from a frozen stock. Undifferentiated human ES cells from a frozen stock vial were resuspended in ES medium with LIF. The ES cell medium consisted of Dulbecco's modified Eagles medium (DMEM), supplemented with 20% ES cell qualified fetal bovine serum (FBS) (Hyclone)), 1% non essential amino acid (NEAA) solution, 2 mM L-glutamine, 0.1 mM β-mercaptoethanol, 50 U/ml penicillin, and 1000 U/ml LIF. The cells were pelleted and plated on mouse feeder layers on a gelatin-coated plastic culture dish using ES medium. The ES cell medium consisted of DMEM with high glucose supplemented with 10-20% FCS, 2 mM L-glutamine, 1% MEM non-essential amino acid solution, 0.1 mM β-mercaptethanol, 50 U/ml pencillin, 50 µg/ml streptomycin, 1000 U/ml LIF, and 4 ηg/ml bFGF, according to the method described by Thomson et al., 1998, Science 282:1145-1147; Shamblott et al., 1998. Proc. Natl. Acad. Sci. USA. 95:13726-13731; and Reubinoff et al., 2000. Nature Biotech. 18:399-403.

The human ES cells were expanded by culturing and regularly passaging the ES cells to inhibit differentiation. The ES cells were passaged by first washing the cells with $Ca^{++}$ and $Mg^{++}$ free Dulbecco's phosphate buffer saline solution for 10 seconds and then treating the cells with 0.05% trypsin for 5 seconds. After 5 seconds, the activity of trypsin was inhibited by adding ES medium containing serum. Next, the cells were scraped and broken down into small clusters. The clusters were then plated onto two 0.1% gelatin coated 100 mm petridish coated with feeder cells in ES medium with LIF and bFGF, as described above. The cells were expanded for 4-6 days.

3) Generation of Embryoid Bodies:

After the undifferentiated human ES cells were proliferated and expanded, they were cultured to form embryoid bodies. First, the ES cells were dissociated with 0.05% trypsin-EDTA, followed by scraping and breakdown of the cells into small clusters. These clusters were then plated at a density of approximately $1\times10^5$ cells/ml onto bacteriological dishes in the absence of feeder cells. The bacteriological dishes used have a non-adhesive surface that prevents attachment, thereby stimulating differentiation of the ES cells and formation of embryoid bodies. These cells were cultured as a suspension culture in ES medium without LIF and bFGF. The ES medium used to culture these cells had DMEM with high glucose or knockout DMEM which was supplemented with 10-20% FCS or knockout serum replacement, as well as other supplements such as β-mercaptoethanol, L-glutamine, and antibiotics. No bFGF was added to the ES medium. The embryoid bodies were allowed to grow for 4-8 days. During this time, the ES medium was changed every 2 days by a sedimentation method. This sedimentation method was performed by transferring the suspension of aggregates to a centrifuge tube, allowing the aggregates to settle to the bottom of the tube, aspirating the medium, and replacing it with fresh medium. The aggregates in fresh medium were then returned to the culture dishes. At the end of the 4-8 days, the embryoid bodies were collected and spun down at low speed and resuspended in ES cell medium. About 20-30 embryoid bodies were then plated on a tissue culture plate coated with 0.1% gelatin in ES medium without LIF and incubated for 24 hours.

4) Selection and Expansion of Nestin-Positive Neuroprogenitor Cells:

After 24 hours, nestin-positive cells (neuroprogenitor cells) were selected by replacing the ES medium with ITSFn (nestin selection) serum-free defined medium. The ITSFn medium consisted of DMEM:F12 medium (Gibco) supplemented with the growth factors insulin (5-25 µg/ml) (Sigma), sodium selenite (10-50 nM) (Sigma), transferrin (1-10 µg/ml) (Gibco), and fibronectin (1-5 µg/ml). This medium allows for the selection of nestin-positive cells, and is carried out for 6-10 days, usually 8-9 days, with the ITSFn medium being replenished every 2 days. After complete selection, the neuroprogenitor cells were characterized for nestin expression using an immunofluorescence technique, which showed that approximately 95% of the cells expressed nestin (FIG. 1A).

The nestin-positive cells were subsequently expanded or sorted using magnetic cell sorting (MACS) for enrichment of neural cell adhesion molecule (NCAM) positive cells.

5) Sorting of NCAM-Positive Cells by Magnetic Sorting:

Next, nestin-positive cells were isolated and subjected to expansion or magnetic cell sorting (MACS) for enrichment of neural cell adhesion molecule (NCAM) positive cells. NCAM is a neuron specific surface marker. To sort the nestin-positive cells by MACS using NCAM, the nestin-positive cells were first harvested from the tissue culture plates by incubating the cells with 0.05% trypsin-EDTA. Next, the dissociated live cells were washed with PBS and stained with an antibody against the surface marker NCAM (Chemicon) for 30 minutes. The cells were then incubated with MACS goat anti-rabbit IgG microbeads (Miltenyi Biotec) for 15 minutes. The cells were subjected to magnetic sorting after washing carefully with PBS. To sort the cells, the magnetically labeled cell suspension (approximately $2\times10^8$ cells) was pipetted onto a MACS MS Separation Column (Miltenyi Biotec), and the cells were allowed to flow through the column, and the effluent (negative fraction) was collected. The positive fraction with the NCAM-positive cells was then collected by elution with PBS.

Before immunosorting, the nestin-positive cells were analyzed by FACS, and about 50-60% of the nestin-positive cells expressed the neural surface marker NCAM (FIGS. 2A and 2B). After immunosorting by MACS, the population of viable nestin-positive cells expressing NCAM was enriched to about 80-85% (FIGS. 3A and 3B).

6) Expansion of NCAM-Positive Neuroprogenitor Cells:

The isolated NCAM-positive cells were expanded by first dissociating the cells with 0.05% trypsin-EDTA, and then plating the cells onto poly-L-Ornithine/laminin coated plates containing expansion medium. Culturing the NCAM-positive cells in this manner permits better adhesion and proliferation in the expansion medium. The expansion medium included DMEM:F12, insulin (10-100 µg/ml), sodium selenite (10-50 nM), Transferrin (1-10 mg/ml), Putrescine (50-200 µM), Progesterone (5-40 nM), and Laminin (10-50 µg/ml). Two or more growth factors such as bFGF (10-50 ng/ml), EGF (10-50 ng/ml), BDNF (50-200 ng/ml), FGF-8 (50-200 ng/ml), and/or SHH (200-400 ng/ml) were also included in the serum-free expansion medium. These various factors present in the expansion medium contribute to the overall increase in the percentage of neuronal cells and further induce these midbrain neuronal precursor cells to adopt the dopaminergic phenotype. The expansion medium was replenished every 2 days, and the nestin-positive, NCAM-positive cells were allowed to proliferate for 6-10 days (FIG. 1B).

Under these culture conditions, about 50-60% of the cells extended neurite processes and stained positive for NCAM, which evidenced their ability to form neurons (FIG. 3). These cells were also immunoreactive to early neuronal marker β-tubulin (FIG. 4B). These neuroprogenitor cells were then serially passaged, and Applicants observed that these neuroprogenitor cells can be passaged up to 10 times and still maintain the capability to differentiate into dopaminergic neurons, without any apparent effect on the potential of the cells to differentiate into committed matured dopaminergic neurons.

7) Differentiation and Maturation of Dopaminergic Neurons:

Development of dopaminergic neurons in vivo depends on the regulated action of extracellular signaling molecules. These molecules activate a cascade of transcription factors with lineage-restricted expression. These transcription factors are responsible for increasing the expression of a specific set of genes involved in the development of the dopaminergic phenotype. To encourage the expanded neuroprogenitors cells generated using the above protocol into functional dopaminergic neurons, the growth factors bFGF and EGF were first withdrawn from the cells. Next, differentiation of the neuroprogenitors cells into dopaminergic neurons was induced by culturing the cells in Neurobasal medium for 30-50 days. The Neurobasal medium included Neurobasal A medium (Gibco), FCS (10-20%) (HYCLONE), and B27 (2-10%) (Gibco), as well as various growth factors. The growth factors included in this medium were Interleukin-1β (IL-1β) (1-2 µg/ml) (Sigma), ascorbic acid (50-150 nM) (Sigma), N-acetyl cysteine (50-150 nM) (ICN), db-cAMP (500-1000 µM) (Sigma), GDNF (1-5 µg/ml) (Sigma), TGF-β3 (1-5 µg/ml) (Sigma), Neurturin (100-500 µg/ml) (Chemicon), BDNF (50-200 ng/ml) (Sigma), FGF-8 (50-200 ng/ml) (R&D Systems), and/or SHH (200-400 ng/ml) (R&D Systems). The Neurobasal medium was sterile filtered with a 0.22 µmillipore syringe filter.

Tyrosine hydroxylase (TH) is the rate limiting enzyme for dopamine synthesis. Certain lineage-restricted growth factors promote the induction of TH synthesis. Addition of these factors to the medium resulted in a higher percentage of cells adopting the dopaminergic phenotype. These factors were added at different time points during neuronal differentiation, as indicated in Table 1. IL-1β, which is present in the Neurobasal medium, appears to play a key role in the differentiation of neuroprogenitors to dopaminergic neurons. Although not wishing to be limited to any particular mechanism, IL-1β appears to increase the amount of TH positive neurons, as well as the responsiveness of the cells to signaling molecules in the medium. The application of these growth factors is combined with changing the Neurobasal medium every 3 days during tissue culture period of 30-50 days.

The cocktail of growth factors in the Neurobasal medium added at different days during differentiation of neuroprogenitor cells is depicted in Table 1 below:

TABLE 1

Differentiation conditions for neuroprogenitor cells
Culture condition for differentiation

| Days 1-4 | Days 4-7 | Days 8-50 | TH positive cells (%) |
|---|---|---|---|
| Neurobasal medium, FCS, B27, IL-1β | Neurobasal medium, FCS, B27, Shh, FGF-8 IL-1β, db-cAMP, GDNF, BDNF | Neurobasal medium, FCS, B27, Shh, FGF-8 IL-1β, db-cAMP, GDNF, BDNF, TGF-β3, neurturin | 65% |
| Neurobasal medium, FCS, B27, IL-1β | Neurobasal medium, FCS, B27, Shh, FGF-8 IL-1β, db-cAMP, GDNF, BDNF | Neurobasal medium, FCS, B27, Shh, FGF-8, IL-1β, db-cAMP, GDNF, BDNF, TGF-β3, neurturin | 55% |
| Neurobasal medium, FCS, B27, IL-1β | Neurobasal medium, FCS, B27, Shh, FGF-8, IL-1β, db-cAMP, GDNF, Shh, FGF-8, BDNF, ascorbic acid | Neurobasal medium, Shh, FGF-8, FCS, B27, IL-1β, db-cAMP, GDNF, BDNF, TGF-β3, neurturin, ascorbic acid | 42% |
| Neurobasal medium, FCS, B27, IL-1β | Neurobasal medium, Shh, FGF-8, FCS, B27, IL-1β, db-cAMP, GDNF, BDNF, N-acetyl cysteine | Neurobasal medium, Shh, FGF-8, FCS, B27, IL-1β, db-cAMP, GDNF, BDNF, TGF-β3, neurturin, N-acetyl cysteine, | 64% |
| Neurobasal medium, FCS, B27 | Neurobasal medium, FCS, B27 | Neurobasal medium, FCS, B27 | 20% |

When the ES cells are induced to differentiate using the Neurobasal medium, the ES cells develop into a variety of neuronal cell types, including dopaminergic neurons, serotonergic neurons, and oligodendrocytes (FIGS. 5, 6, and 7). While the percentage of cells that differentiate into dopaminergic neurons remains relatively low in standard culture conditions, supplementing the media with the growth factors as shown in Table 1 resulted in an increase in the percentage of dopaminergic neurons generated. For example, over 60% of the ES cells differentiated into cells that were positive for TH, a specific marker for dopaminergic neurons.

8) Characterization of Differentiated Neurons

The differentiated neuronal cell types generated according to the present disclosure were evaluated both by the overall morphology of the cells, as well as the phenotypes identified by immunoflourescence. Immunoflourescence analysis was carried out at the neuroprogenitor expansion stage (expansion of NCAM positive cells), and various other time points of differentiation using standard protocols well known to those of skill in the art. First, the isolated cells were grown in 2-well chamber slides precoated with extracellular matrices, rinsed with PBS, and fixed for 10 minutes with 4% paraformaldehyde at room temperature. Next, the cells were permeabilized with 0.2% Triton X-100 in PBS for 5 minutes, blocked with 1% bovine serum albumin (BSA)/PBS for 2 hours, and incubated with a primary antibody (antibody dilution was made in 1% BSA/TBS) overnight at 4° C. The cells were stained with the following primary antibodies: early neuronal marker β-Tubulin, NCAM, Neurofilament, late neuronal marker Microtubule associated protein 2 (MAP-2), neuron cell surface antigen A2B5, Nurr-1, Tyrosine hydroxylase, the dopamine transporter DAT, dopamine β-hydroxylase (DBH), the astrocyte marker glial fibrillary acidic protein (GFAP), GABA, Oligodendrocyte, Serotonin, and Synaptophysin, all of which were obtained from CHEMICON. Finally, the cells were incubated with an FITC labeled secondary antibody. After each of the above steps, the cells were washed three times with PBS.

The chamber slides were observed under the fluorescence microscope to evaluate the immunopositive areas. This immunofluorescence analysis demonstrated that a large percentage of the differentiated cells were immunoreactive to the neuron specific markers NCAM (FIG. 3), MAP-2 (FIG. 4A), and β-Tubulin (FIG. 4B). The expression of these key antigens increased with greater incubation times in the differentiation medium. Immunofluorescence analysis also demonstrated that a smaller percentage of the cells expressed serotonin (FIG. 7), as well as the non-neuronal markers glial fibrillary acidic protein (GFAP), which is present in astrocytes, and GABA and glutamate, which is present in Oligodendrocyte (FIG. 6).

The differentiated cells were also analyzed by double-labeling the cells with primary antibodies to TH (green), along with MAP-2, DAT, Nurr-1, β-Tubulin, FITC-labeled secondary antibodies (Texas red) respectively (FIG. 8). This analysis demonstrated that the proportion of MAP-2 positive cells expressing TH was higher. The cell density of dopaminergic neurons was quantified by counting the numbers of TH-positive cells and MAP-2-positive cells per field in randomly selected fields using a 40× objective lens. The percent proportion of TH-positive cells was calculated (FIG. 9). TH-positive neurons also expressed Nurr-1 and DAT, but there was no colocalization of TH with DBH, which confirmed the dopaminergic phenotype of the cells. Additionally, synapse formation was identified by immunostaining with synaptophysin.

Immunofluorescence analysis also showed that the percentage of sorted NCAM-positive cells expressing TH is about 60%, while about 30% express serotonin (FIG. 10). In addition, about 40% of the nestin-positive cells stained positively for TH, about 30% stained positively for Serotonin, and about 28% stained positively for Oligodendrocyte (FIG. 11). Immunological markers used at different stages of differentiation are shown in Table 3 and indicate the phenotypic characteristics of undifferentiated and differentiated ES cells:

TABLE 3

Phenotypic characteristics of undifferentiated and differentiated ES cells

| Undifferentiated ES colonies | Neuronal cells | Dopaminergic neurons | Glial cells |
|---|---|---|---|
| SSEA-1 | NCAM | Nurr1 | A2B5 |
| SSEA-3 | β tubulin | TH | GFAP |
| SSEA-4 | Neurofilament | DAT | O4 |
| Tra-1-60 | A2B5 | DBH | |
| Tra-1-81 | MAP-2 | | |
| Oct-4 | Serotonin | | |
| GCTM-2 | GABA | | |
| CD-30 | Synaptophysin | | |
| cripto-1 | | | |
| GCNF | | | |
| c-Kit | | | |

9) Gene Expression Profile

The gene expression profile of cells collected at different stages was also analyzed. Cells were collected for analysis by Reverse Transcriptase Polymerase Chain Reaction (RT-PCR) from each of the following stages of the disclosed method: undifferentiated ES cells, embryoid bodies, Nestin-positive neuroprogenitor cells, NCAM-positive cells, and differentiated cells isolated after 12, 17, 22, 27, and 37 days of differentiation in Neurobasal medium. After the cells were collected they were pelleted, and total cellular RNA was extracted from the cell pellets using the RNeasy Qiagen kit. The isolated RNA was stored at −20° C.

cDNA was synthesized from the isolated total RNA using Moloney Leukemia virus superscript II reverse transcriptase and Oligo $(dT)_{12-18}$ The cDNA synthesized by this reverse transcriptase reaction was used for PCR amplification with different sets of specific primers to determine which genes were expressed in the collected cells. These PCR reactions were carried out using the cDNA as the template and platinum Taq polymerase under standard PCR conditions, which are well known to those of skill in the art. The general cycling parameters used to amplify DNA products were as follows:
1. denaturation of the template cDNA at 94° C. for 30 seconds;
2. annealing the primers at 55-65° C. for 1 minute, depending on the primers used; and
3. incubating the reaction at 72° C. for 1 minute, and repeating steps 1-3 (cycles) between 25 and 40 times.

After the PCR reaction, the products were run through an 1.5% agarose gel using electrophoresis along with a DNA size ladder. The expression of TH, D2RL, DBH, En-1, Nurr-1, and β-tubulin were all analyzed by RT-PCR using the primers as set forth in Table 4:

TABLE 4

Primer sets used to amplify dopamine-specific genes

| Gene | Primer Sequence | |
|---|---|---|
| TH (417 bp) | TGT CAG AGC AGC CCG AGG TC | (SEQ ID NO:1) |
| | CCA AGA GCA GCC CAT CAA AG | (SEQ ID NO:2) |
| D2RL (404 bp) | GCA GTC GAG CTT TCA GAG CC | (SEQ ID NO:3) |
| | TCT GCG GCT CAT CGT CTT AAG | (SEQ ID NO:4) |
| DBH (447 bp) | CAC GTA CTG GTG CTA CAT TAA GGA GC | (SEQ ID NO:5) |
| | AAT GGC CAT CAC TGG CGT GTA ACA CC | (SEQ ID NO:6) |

TABLE 4-continued

Primer sets used to amplify dopamine-specific genes

| Gene | Primer Sequence | |
|---|---|---|
| En-1 (390 bp) | TGG TCA AGA CTG ACT CAC AGC A | (SEQ ID NO:7) |
|  | TCT CGT CTT TGT CCT GAA CCG T | (SEQ ID NO:8) |
| Nurr1 (255 bp) | TGA AGA GAG CGG AGA AGG AGA T | (SEQ ID NO:9) |
|  | TCT GGA GTT AAG AAA TCG GAG CT | (SEQ ID NO:10) |
| β-tubulin (317 bp) | GGA ACA TAG CCG TAA ACT GC | (SEQ ID NO:11) |
|  | TCA CTG TGC CTG AAC TTA CC | (SEQ ID NO:12) |

The above analysis by RT-PCR demonstrated that the expression of the dopaminergic phenotype specific gene, TH, was seen after neuronal differentiation of the ES cells until terminal differentiation into dopaminergic neurons (FIG. 12). As expected, β-tubulin, a ubiquitously expressed gene, was seen in all cell samples, while DBH was not expressed in any cell samples.

10) Reverse Phase HPLC for Dopamine Detection

One definitive characteristic of a dopaminergic neuron is the production of dopamine. Therefore, the functional capacity of embryonic stem cell-derived dopaminergic neurons to produce dopamine was evaluated by directly measuring the intracellular dopamine levels using Reverse Phase HPLC (RP-HPLC). The concentration of dopamine detected in each sample was determined by comparison with a standard solution of dopamine injected into the column immediately before and after each experiment.

To begin, cells were collected at different stages of the disclosed method: undifferentiated ES cells, embryoid bodies, Nestin-positive neuroprogenitor cells, NCAM-positive cells, and differentiated cells isolated after 7, 22, and 37 days of differentiation in Neurobasal medium. Before collection, the cells differentiated in Neurobasal medium were first stimulated to induce dopamine secretion by the addition of 56 mM KCl in HBSS for 15 minutes. Approximately $5\times10^6$ cells were trypsinised and pelleted by centrifugation. The cells were then sonicated in cold 1N perchloric acid with antioxidants (0.2 g/l sodium metabisulphite), and centrifuged at 15,000 rpm/min for 20 minutes at 4° C. The supernatent was extracted and stored at −70° C. for subsequent determination of the intracellular dopamine concentration by RP-HPLC. Dopamine levels were determined in the cell lysates and culture supernatent (48 hrs after the last medium change). The culture supernatent was immediately stabilized with 7.5% orthophosphoric acid and sodium metabisulphite.

The cell lysates analyzed by RP-HPLC from earlier stages of the disclosed method, such as undifferentiated ES cells, embryoid bodies, Nestin-positive neuroprogenitor cells, and NCAM-positive cells, did not contain any detectable levels of dopamine. After the first week of differentiation in Neurobasal medium, however, the cell lysates analyzed by RP-HPLC all contained dopamine. The level of intracellular dopamine significantly increased as the number of dopaminergic neurons in the cell lysate increased and terminally matured over time in the differentiation Neurobasal medium. The intracellular level of dopamine was even higher in the cell cultures that were treated with growth factor versus untreated cultures at the indicated time points as shown in FIG. 13. Further confirmation of the production of dopamine by these cell culture was shown after incubation of cell cultures with N-methyl-4-phenyl 1,2,3,6 -tetrahydropyridine hydrochloride (MPTP), a neurotoxin that targets dopaminergic neurons. In the cell cultures incubated with MPTP, no dopamine was detected in the cell lysates by RP-HPLC analysis. In contrast, dopamine release into the conditioned medium was increase in cell cultures stimulated with 56 mM KCL (FIG. 14). Adding an array of growth factors to the differentiation Neurobasal medium also increased intracellular dopamine level of the cell lysates (Table 5).

TABLE 5

Dopamine concentration (μg/ml) in cell lysates by HPLC

| | | Days of differentiation | | |
|---|---|---|---|---|
| # | Culture conditions for differentiation | 7 d | 22 d | 37 d |
| 1 | Absence of growth factors | 0.5 | 1.3 | 1.1 |
| 2 | Addition of growth factors | 5.0 | 21.5 | 5.5 |
| 3 | Stimulation with 56 mM KCl | 5.5 | 22 | 7.2 |
| 4 | N-acetyl cysteine along with growth factors | 4.93 | 20.9 | 9 |
| 5 | Stimulation with 56 mM KCl | 8.8 | 30.9 | 10 |
| 6 | Ascorbic acid along with growth factors | 6.2 | 3.7 | 9.7 |
| 7 | Stimulation with 56 mM KCl | 6.9 | 5.5 | 10 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of generating a differentiated neural cell population from primate pluripotent stem cells comprising the following steps:
   (a) expanding a culture of primate pluripotent stem cells;
   (b) culturing the pluripotent stem cells to select for neuroprogenitor cells that are positive for nestin;
   (c) sorting the nestin-positive neuroprogenitor cells for enrichment of NCAM-positive cells;
   (d) differentiating the nestin-positive, NCAM-positive cells to generate a differentiated neural cell population by culturing the cells in a differentiation media which comprises N-acetyl cysteine and TGF-β3 or interleukin-1β or both, wherein the differentiated neural cell population comprises at least about 60% dopaminergic neurons or at least about 30% serotonergic neurons.

2. The method of claim 1, wherein the pluripotent stem cells were derived using a laser ablation technique.

3. The method of claim 1, wherein the pluripotent stem cells are human embryonic stem cells.

4. The method of claim 3, wherein the human embryonic stem cells were derived using a laser ablation technique.

5. The method of claim 1, wherein the differentiated neural cell population comprises at least about 60% dopaminergic neurons and at least about 30% serotonergic neurons.

6. The method of claim 1, further comprising culturing the pluripotent stem cells of step (b) to form embryoid bodies.

7. The method of claim 6, wherein the embryoid bodies are cultured to select for neuroprogenitor cells that are positive for nestin.

8. The method of claim 1, wherein the neuroprogenitor cells that are positive for nestin are selected by culturing the pluripotent stem cells in serum-free medium.

9. The method of claim 8, wherein the serum-free medium is ITSFn serum-free defined medium.

10. The method of claim 8, wherein the serum-free medium comprises one or more soluble factors selected from the group consisting of insulin, sodium selenite, transferrin, and fibronectin.

11. The method of claim 10, wherein the serum-free medium comprises insulin, sodium selenite, transferrin, and fibronectin.

12. The method of claim 7, wherein the neuroprogenitor cells that are positive for nestin are selected by culturing the embryoid bodies in serum-free medium.

13. The method of claim 12, wherein the serum-free medium is ITSFn serum-free defined medium.

14. The method of claim 12, wherein the serum-free medium comprises one or more soluble factors selected from the group consisting of insulin, sodium selenite, basic fibroblast growth factor, transferrin, and fibronectin.

15. The method of claim 14, wherein the serum-free medium comprises insulin, sodium selenite, transferrin, and fibronectin.

16. The method of claim 15, wherein the neuroprogenitor cells comprise at least about 95% nestin-positive cells.

17. The method of claim 1, wherein the nestin-positive neuroprogenitor cells of step (c) are sorted to enrich for NCAM-positive cells by Magnetic Cell Sorting (MACS).

18. The method of claim 17, wherein the nestin-positive neuroprogenitor cells comprise at least about 50-60% NCAM-positive cells.

19. The method of claim 1, further comprising expanding the nestin-positive, NCAM-positive neuroprogenitor cells of step (c) in expansion medium.

20. The method of claim 19, wherein the expansion medium comprises one or more soluble factors selected from the group consisting of insulin, sodium selenite, transferrin, laminin, putrescine, progesterone, basic fibroblast growth factor (bFGF), epidermal growth factor (EGF), sonic hedgehog (SHH), fibroblast growth factor-8 (FGF-8), and brain derived neurotropic factor (BDNF).

21. The method of claim 20, wherein the nestin-positive, NCAM-postive cells are grown in the expansion medium for 6-10 days.

22. The method of claim 20, wherein the nestin-positive, NCAM-postive cells are cultured and serially passed for one or more population doublings.

23. The method of claim 20, wherein the nestin-positive, NCAM-postive cells are cryopreserved in liquid nitrogen.

24. The method of claim 1, wherein the differentiation media comprises Neurobasal medium supplemented with fetal calf serum, B27, ascorbic acid, and N-acetyl cysteine.

25. The method of claim 1, wherein the differentiation media further comprises one or more differentiation agents selected from the group consisting of ascorbic acid, glial cell line derived neurotropic factor (GDNF), dibutyrl-cyclic AMP (db-cAMP), brain derived neurotropic factor (BDNF), neuturin, sonic hedgehog protein (SHH), and fibroblast growth factor-8 (FGF-8).

26. The method of claim 1, wherein the nestin-positive, NCAM-positive cells are grown in differentiation media for 30-50 days.

27. A method of generating dopaminergic neurons from neuroprogenitor cells, comprising enriching the neuroprogenitor cells for cells that are positive for nestin and positive for NCAM, and differentiating the nestin-positive, NCAM-positive cells to generate dopaminergic neurons by culturing the cells in the presence of N-acetyl cysteine and TGF-β3 or interleukin-1β or both, wherein at least about 60% of the nestin-positive, NCAM-positive cells differentiate into dopaminergic neurons.

28. A method of generating serotonergic neurons from neuroprogenitor cells, comprising enriching the neuroprogenitor cells for cells that are positive for nestin and NCAM, and differentiating the nestin-positive, NCAM-positive cells to generate serotonergic neurons by culturing the cells in the presence of N-acetyl cysteine and TGF-β3 or interleukin-1β or both, wherein at least about 30% of the nestin-positive, NCAM-positive cells differentiate into serotonergic neurons.

* * * * *